United States Patent
Lowery et al.

(10) Patent No.: US 12,171,735 B2
(45) Date of Patent: *Dec. 24, 2024

(54) ADMINISTRATION OF BUTYRATE, BETA-HYDROXYBUTYRATE, CANNABIDIOL, AND RELATED COMPOUNDS IN HUMANS

(71) Applicant: AXCESS GLOBAL SCIENCES, LLC, Salt Lake City, UT (US)

(72) Inventors: Ryan Lowery, Tampa, FL (US); Jacob Wilson, Tampa, FL (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/711,561

(22) Filed: Apr. 1, 2022

(65) Prior Publication Data

US 2022/0362188 A1 Nov. 17, 2022

Related U.S. Application Data

(63) Continuation of application No. 16/667,851, filed on Oct. 29, 2019, now abandoned, and a continuation of application No. 17/367,206, filed on Jul. 2, 2021, which is a continuation of application No. 15/491,924, filed on Apr. 19, 2017, now Pat. No. 11,173,138.

(60) Provisional application No. 62/752,170, filed on Oct. 29, 2018.

(51) Int. Cl.
| | |
|---|---|
| *A61K 31/195* | (2006.01) |
| *A61K 9/14* | (2006.01) |
| *A61K 9/48* | (2006.01) |
| *A61K 31/352* | (2006.01) |
| *A61K 31/4375* | (2006.01) |
| *A61P 3/00* | (2006.01) |

(52) U.S. Cl.
CPC .............. *A61K 31/195* (2013.01); *A61K 9/14* (2013.01); *A61K 9/4808* (2013.01); *A61K 31/352* (2013.01); *A61K 31/4375* (2013.01); *A61P 3/00* (2018.01)

(58) Field of Classification Search
CPC ................ A61K 31/195; A61K 31/352; A61K 31/4375; A61K 9/0053; A61K 9/14; A61K 9/4808; A61P 3/00
See application file for complete search history.

(56) References Cited

U.S. PATENT DOCUMENTS

| | | | |
|---|---|---|---|
| 6,207,856 B1 | 3/2001 | Veech | |
| 6,380,244 B2 | 4/2002 | Martin | |
| 7,807,718 B2 | 10/2010 | Hashim et al. | |
| 8,071,641 B2 | 12/2011 | McWhorter | |
| 8,642,654 B2 | 2/2014 | Clarke | |
| 10,245,242 B1 | 4/2019 | Millet | |
| 10,245,243 B1 | 4/2019 | Millet | |
| 10,278,961 B2 | 5/2019 | Lowery et al. | |
| 11,026,929 B2 | 6/2021 | Lowery et al. | |
| 2002/0013339 A1 | 1/2002 | Martin et al. | |
| 2002/0124370 A1 | 9/2002 | Deckert et al. | |
| 2009/0306221 A1 | 12/2009 | Guy | |
| 2010/0113494 A1 | 5/2010 | Hu et al. | |
| 2014/0350105 A1 | 11/2014 | D'Agostino | |
| 2015/0063140 A1 | 3/2015 | Yi et al. | |
| 2015/0065571 A1 | 3/2015 | Clarke et al. | |
| 2016/0272603 A1 | 9/2016 | Kravchenko et al. | |
| 2017/0296501 A1 | 10/2017 | Lowery | |
| 2017/0296520 A1 | 10/2017 | Lowery et al. | |
| 2018/0020699 A1 | 1/2018 | Steup | |
| 2018/0021274 A1 | 1/2018 | Arnold | |
| 2019/0255028 A1 | 8/2019 | Lowery et al. | |
| 2019/0313682 A1 | 10/2019 | Nagel | |
| 2020/0061004 A1 | 2/2020 | Millet | |
| 2020/0129463 A1 | 4/2020 | Lowery et al. | |
| 2022/0133673 A1 | 5/2022 | Millet | |

FOREIGN PATENT DOCUMENTS

| | | |
|---|---|---|
| CN | 1104978 C | 4/2003 |
| CN | 1184978 C | 1/2005 |
| EP | 1755743 B1 | 4/2013 |
| JP | 5690261 B2 | 3/2015 |
| WO | 00/04895 A2 | 2/2000 |
| WO | 00/15216 A1 | 3/2000 |
| WO | 2005/077348 A1 | 8/2005 |
| WO | 2006/029577 A1 | 3/2006 |
| WO | 2007/138322 A1 | 12/2007 |
| WO | 2008/021394 A2 | 2/2008 |
| WO | 2010/021766 A1 | 2/2010 |

(Continued)

OTHER PUBLICATIONS

Newman et al. (Annu Rev Nutr 2017) (Year: 2017).*
Newman et al. (Diabetes Res Clin Pract 2014) (Year: 2014).*
Dedkova (Frontiers in Physiology, Jul. 2014) (Year: 2014).*
International Search Report and Written Opinion received for PCT Patent Application No. PCT/US2023/020407, mailed on Jul. 26, 2023, 10 pages.
International Search Report and Written Opinion received for PCT Patent Application No. PCT/US2023/020417, mailed on Jul. 21, 2023, 11 pages.
Office Action received for European Patent Application No. 17786592. 0, mailed on Jun. 17, 2022, 7 pages.
Office Action received for European Patent Application No. 17786592. 0, mailed on Sep. 25, 2020, 7 pages.
Stefan et al., "The Effects of Exogenous Beta-Hydroxybutyrate Supplementation on Metrics of Safety and Health", International Journal of Nutrition and Food Sciences, vol. 9, No. 6, Nov. 2020, pp. 154-162.

(Continued)

*Primary Examiner* — Umamaheswari Ramachandran
(74) *Attorney, Agent, or Firm* — Workman Nydegger

(57) ABSTRACT

In various implementations, cannabidiol, beta-hydroxybutyrate, related compounds, and/or one or more other compounds may be administered to an individual to improve the health of the individual. The beta-hydroxybutyrate may include R-beta-hydroxybutyrate. The beta-hydroxybutyrate may include a salt and a polymer of beta-hydroxybutyrate. Other compounds may include amino acids, fatty acids or esters thereof, and/or combinations thereof.

18 Claims, 12 Drawing Sheets

(56) References Cited

FOREIGN PATENT DOCUMENTS

| WO | 2010/104595 A1 | 9/2010 |
|----|----------------|--------|
| WO | 2012/024611 A1 | 2/2012 |
| WO | 2014/153415 A2 | 9/2014 |
| WO | 2014/153416 A1 | 9/2014 |
| WO | 2015/063140 A1 | 5/2015 |
| WO | 2017/156446 A1 | 9/2017 |
| WO | 2017/184788 A1 | 10/2017 |
| WO | 2018/132189 A1 | 7/2018 |
| WO | 2019/200132 A1 | 10/2019 |
| WO | 2020/092451 A1 | 5/2020 |
| WO | 2022/040644 A2 | 2/2022 |

OTHER PUBLICATIONS

Supplementary European Search Report received for EP Patent Application No. 17786592.0, mailed on Nov. 25, 2019. 10 pages.
Allendorfer et al., "Neuroimaging studies towards understanding the central effects of pharmacological cannabis products on patients with epilepsy", Epilepsy Behav, May 2017, vol. 70, pp. 349-354.
European Search Report received for EP Patent Application No. 19880284.5, mailed on Jul. 12, 2022, 11 pages.
International Preliminary Report on Patentability received for PCT Patent Application No. PCT/US17/28465, mailed on Nov. 1, 2018, 7 pages.
International Preliminary Report on Patentability received for PCT Patent Application No. PCT/US17/28466, mailed on Nov. 1, 2018, 8 pages.
International Preliminary Report on Patentability received for PCT Patent Application No. PCT/US19/58676, mailed on May 14, 2021, 6 pages.
International Search Report and Written Opinion received for PCT Patent Application No. PCT/US17/28466, mailed on Jul. 5, 2017, 8 pages.
International Search Report and Written Opinion received for PCT Patent Application No. PCT/US19/58676, mailed on Jan. 16, 2020, 6 pages.
International Search Report and Written Opinion received for PCT Patent Application No. PCT/US22/36030, mailed on Oct. 7, 2022, 7 pages.
International Search Report and Written Opinion received for PCT Patent Application No. PCT/US17/28465, mailed on Jul. 5, 2017, 7 pages.
Lannotti et al., "Effects of non-euphoric plant cannabinoids on muscle quality and performance of dystrophic mdx mice", Br J Pharmacol, May 2019, vol. 176, No. 10, pp. 1568-1584.
Energy Times—"Herbal Keto Support", Jan. 15, 2008 (5 pages).
Decision to grant received for European Patent Application No. 17786592.0, mailed on Nov. 3, 2023, 2 pages.
Intention to grant received for European Patent Application No. 17786592.0, mailed on Jun. 27, 2023, 7 pages.
International Search Report and Written Opinion received for PCT Patent Application No. PCT/US22/49036, mailed on Mar. 8, 2023, 9 pages.
Office Action received for European Patent Application No. 19880284.5, mailed on Nov. 9, 2023, 5 pages.

* cited by examiner

Figure 1

| Subject | Condition | Baseline | 30 minutes | 60 minutes | 90 minutes | 120 minutes | 180 minutes |
|---|---|---|---|---|---|---|---|
| A | 10g DL-BHB | 0.2 | 0.7 | 0.5 | 0.3 | 0.2 | 0.2 |
| B | 10g DL-BHB | 0.1 | 0.9 | 0.6 | 0.3 | 0.2 | 0.2 |
| C | 10g DL-BHB | 0.1 | 0.5 | 0.2 | 0.1 | 0.1 | 0.1 |
| D | 10g DL-BHB | 0.2 | 0.8 | 0.6 | 0.3 | 0.2 | 0.1 |
| Average | | 0.15 | 0.725 | 0.475 | 0.25 | 0.175 | 0.15 |
| A | 10g R-BHB | 0.2 | 1.8 | 0.7 | 0.4 | 0.3 | 0.2 |
| B | 10g R-BHB | 0.2 | 1.5 | 0.7 | 0.3 | 0.2 | 0.2 |
| C | 10g R-BHB | 0.1 | 0.7 | 0.3 | 0.2 | 0.2 | 0.1 |
| D | 10g R-BHB | 0.1 | 1.5 | 1.2 | 0.6 | 0.2 | 0.2 |
| Average | | 0.15 | 1.375 | 0.725 | 0.375 | 0.225 | 0.175 |
| A | 5g R-BHB | 0.3 | 0.6 | 0.3 | 0.4 | 0.3 | 0.4 |
| B | 5g R-BHB | 0.1 | 0.8 | 0.7 | 0.2 | 0.2 | 0.2 |
| C | 5g R-BHB | 0.1 | 0.4 | 0.2 | 0.2 | 0.2 | 0.1 |
| D | 5g R-BHB | 0.1 | 0.7 | 0.3 | 0.2 | 0.1 | 0.1 |
| Average | | 0.15 | 0.625 | 0.375 | 0.25 | 0.2 | 0.2 |

Figure 14A
Figure 14B
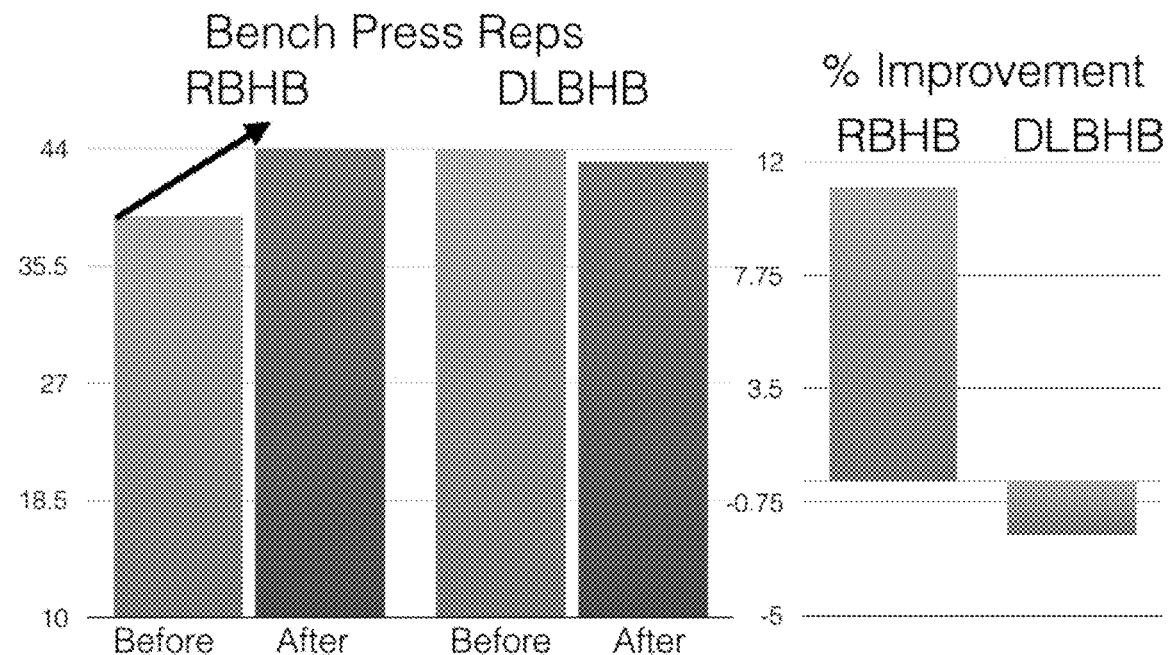
Figure 14C
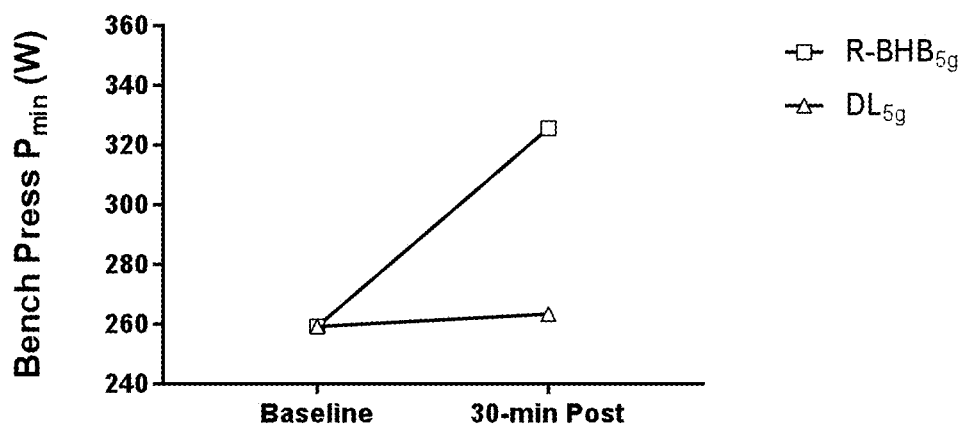

ADMINISTRATION OF BUTYRATE, BETA-HYDROXYBUTYRATE, CANNABIDIOL, AND RELATED COMPOUNDS IN HUMANS

CROSS-REFERENCE TO RELATED APPLICATIONS

This application is a continuation of U.S. patent application Ser. No. 16/667,851, filed on Oct. 29, 2019 and entitled "ADMINISTRATION OF BUTYRATE, BETA-HYDROXYBUTYRATE, CANNABIDIOL, AND RELATED COMPOUNDS IN HUMANS", which claims the benefit of U.S. Patent Application No. 62/752,170, filed on Oct. 29, 2018 and entitled "ADMINISTRATION OF BUTYRATE, BETA-HYDROXYBUTYRATE, CANNABIDIOL, AND RELATED COMPOUNDS IN HUMANS", both of which is incorporated by reference herein for all purposes.

This application is also a continuation of U.S. patent application Ser. No. 17/367,206 filed on Jul. 2, 2021 and entitled "ADMINISTRATION OF R-BETA-HYDROXYBUTYRATE AND RELATED COMPOUNDS IN HUMANS", which is a continuation in part of U.S. patent application Ser. No. 15/491,924, filed on Apr. 19, 2017 and entitled "ADMINISTRATION OF R-BETA-HYDROXYBUTYRATE AND RELATED COMPOUNDS IN HUMANS" and now issued as U.S. Pat. No. 11,173,138, which claims priority to U.S. Provisional Patent Application No. 62/324,798, entitled "ADMINISTRATION OF BUTYRATE, BETA-HYDROXYBUTYRATE, AND RELATED COMPOUNDS IN HUMANS", filed on Apr. 19, 2016, all of which are incorporated by reference herein for all purposes.

TECHNICAL FIELD

The present invention relates to administration of butyrate, beta-hydroxybutyrate, and related compounds with cannabidiol and related compounds.

BACKGROUND

Currently, beta-hydroxybutyrate salts can be administered orally or intravenously in humans to promote weight loss and/or ketosis. However, the excess intake of salts such as sodium, magnesium, and potassium may be unwarranted (e.g., high blood pressure, stroke, damage to organs, gastrointestinal problems, etc.). Thus, many people may not be able to tolerate administration of beta-hydroxybutyrate salts in amounts to promote or sustain weight loss and/or ketosis. Polymers of beta-hydroxybutyrate have also been administered to humans to promote ketosis. However, since polymers must be processed by the body to deliver beta-hydroxybutyrate to the individual, the delivery is slow and/or a larger amount of the polymer must be administered to deliver a specified amount of beta-hydroxybutyrate.

SUMMARY

In various implementations, a pharmaceutically effective amount of: butyrate, beta-hydroxybutyrate, and/or related compounds; cannabidiol and/or related compounds; and/or one or more other compounds may be administered to an individual. For example, a first compound may include pharmaceutically effective amounts of beta-hydroxybutyrate, cannabidiol, and/or one or more other compounds, which may be administered to improve and/or maintain a health of an individual. The administered first compound may cause weight loss, weight maintenance, elevate blood ketone levels, maintain blood ketone levels, reduce blood glucose levels, maintain blood glucose levels, improve focus, improve energy, improve cognitive function, improve traumatic brain injury, improve and/or facilitate maintenance of blood glucose levels, improve and/or facilitate maintenance of diabetes, improve and/or facilitate maintenance of neurological disorders, improve and/or facilitate maintenance of cancer, inflammatory conditions, suppress appetite, reduce and/or slow down the affects of aging, have anti-glycation properties, improve and/or facilitate maintenance of epilepsy, improve and/or facilitate maintenance of neurodegenerative disease(s), improve and/or facilitate maintenance of depression, decrease immune function, facilitate reduction of substance abuse, reduce relapse and/or withdrawal associated with substance abuse, improve performance, improve strength, improve muscle mass, improve fat loss, improve body composition, and/or be used as a medicament etc. The pharmaceutically effective amount of butyrate, beta-hydroxybutyrate, cannabidiol, related compounds (e.g., derivatives, salts, polymers, complexes, etc.), and/or combinations thereof may be administered to healthy individuals and/or not healthy individuals (e.g., with diseases and/or disorders).

Implementations may include one or more of the following features. The beta-hydroxybutyrate included in the first composition may include the racemic mixture and/or the individual isomers of beta-hydroxybutyrate, such as R-beta-hydroxybutyrate (also known as D-beta-hydroxybutyrate). The beta-hydroxybutyrate included the first composition may include related compounds. The beta-hydroxybutyrate included the first composition may include a natural beta-hydroxybutyrate (e.g., produced in nature; and/or by a bacteria, fungus, and/or other microorganism). The beta-hydroxybutyrate included in the first composition may be coupled to a compound such as an amino acid. In some implementations, the beta-hydroxybutyrate administered may include R-beta-hydroxybutyrate and at least one of a polymer of R-beta-hydroxybutyrate or R-beta-hydroxybutyrate-complex. The beta-hydroxybutyrate included in the first composition may include beta-hydroxybutyrate salt and beta-hydroxybutyrate esters, in some implementations. The cannabidiol included in the first composition may include any appropriate form of cannabidiol. The first composition may include other compounds may include short chain fatty acids, short chain triglycerides, medium chain fatty acids, medium chain triglycerides, long chain fatty acids, long chain triglycerides, berberine, berberine metabolites, dihydroberberine, tetrahydroberberine, amino acids such as leucine, and/or combinations thereof.

The first composition may include approximately 0.2 g of to approximately 10 g of beta-hydroxybutyrate. In some implementations, the first composition may include less than approximately 2 g of beta-hydroxybutyrate. The first composition may include R-beta-hydroxybutyrate.

The first composition may include at least approximately 5 mg of cannabidiol. In some implementations, the first composition may include approximately 5 mg to approximately 300 mg of cannabidiol.

The first composition may be administered using any appropriate delivery form, such as tablets, capsules, oils, powders, food product, beverage, etc. The first composition may be unencapsulated and/or encapsulated. The first composition may be administered up to 5 times daily, in some implementations.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIG. 1 illustrates a table of blood ketone levels over time for 4 subjects for an implementation of an example administration of D,L-beta-hydroxybutyrate and R/D-beta-hydroxybutyrate.

FIG. 14A illustrates a chart illustrating strength test results following an implementation of an example administration protocol.

FIG. 14B illustrates a chart illustrating strength test results following an implementation of an example administration protocol.

FIG. 14C illustrates a chart illustrating power test results following an implementation of an example administration protocol.

Like reference symbols in the various drawings indicate like elements.

DETAILED DESCRIPTION

Figure 2:
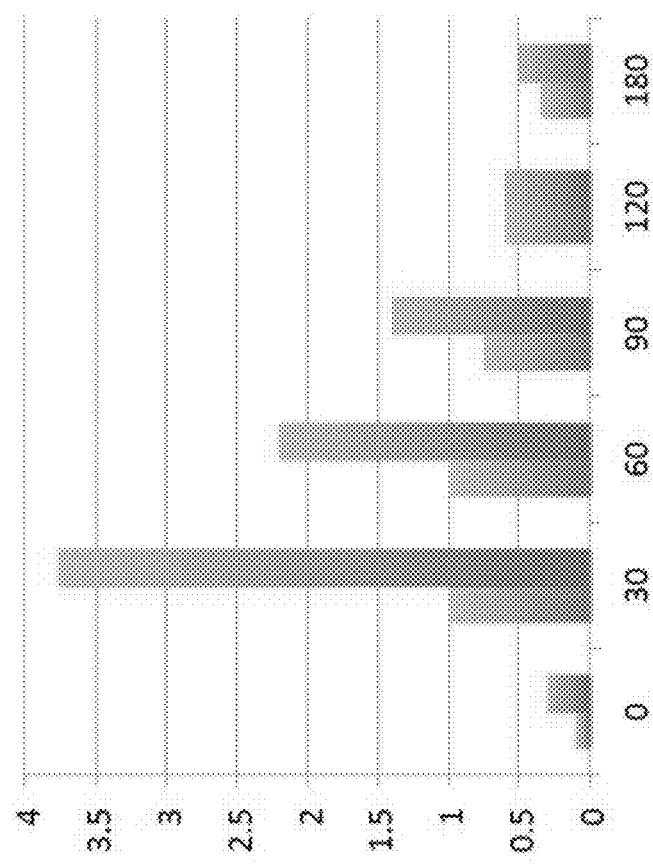
FIG. 2 illustrates a table of blood ketone levels over time for an implementation of an example administration of the microencapsulated butyrate compared to traditional sodium butyrate.

In various implementations, compounds such as butyrate, beta-hydroxybutyrate and/or related compounds (e.g., derivatives, esters, polymers, etc.) may be administered with cannabidiol. This first composition may be administered alone and/or in combination with one or more other compounds.

Administration of a pharmaceutically effective amount of this first composition may improve and/or maintain the health of an individual. For example, administration of a pharmaceutically effective amount of the first composition may promote, improve, and/or maintain: weight loss, ketosis, performance, strength, muscle mass, fat loss, and/or body composition. As another example, administration of a pharmaceutically effective amount of the first composition may suppress appetite. As another example, administration of a pharmaceutically effective amount of the first composition may improve and/or facilitate maintenance of blood ketone levels, blood glucose levels, and/or diabetes. As another example, administration of a pharmaceutically effective amount of the first composition may improve and/or facilitate the maintenance of: neurological disorders (e.g., epilepsy, Parkinson's, Alzheimer's, TBI, ALS, and/or Autism), cancer, inflammatory conditions, and/or depression. As another example, the administration of a pharmaceutically effective amount of the first composition may decrease immune function and/or improve symptoms from diseases associated with overactive immune function. As another example, administration of a pharmaceutically effective amount of the first composition may facilitate substance abuse recovery, such as by reducing the chance of relapse, decreasing cravings, decrease withdrawal side effects, etc.

In various implementations, the first composition may include one or more forms (e.g., salts, derivatives, complexes, compounds, etc,) of cannabidiol, butyrate, and/or beta-hydroxybutyrate.

The cannabidiol ($C_{21}H_{30}O_2$; 2-[(1R,6R)-3-methyl-6-prop-1-en-2-ylcyclohex-2-en-1-yl]-5-pentylbenzene-1,3-diol) may include any appropriate form of cannabidiol (e.g., salts, acids such as cannabidiol acid (CBDa), oils that include CBD, extracts that include CBD, derivatives, analogues, etc). Cannabidiol (CBD) may be derived from the *cannabis* plant, in some implementations. Cannabidiol may be non-psychoactive (e.g., unlike tetrahydrocannabinol (THC), which also may be derived from the *cannabis* plant). Cannabidiol acts on a different aspect of human physiology than butyrate and/or beta-hydroxybutyrate. However, in administration of cannabidiol with butyrate and/or beta-hydroxybutyrate, unexpectedly, the cannabidiol does not compete with impact of butyrate and/or beta-hydroxybutyrate on an individual's health. Additionally, administration of cannabidiol with butyrate and/or beta-hydroxybutyrate provides more than just a cumulative effect of the compounds individually due to the synergistic effect (e.g., cannabidiol increases the impact the butyrate and/or beta-hydroxybutyrate is able to provide). Thus, the combination of cannabidiol with butyrate and/or beta-hydroxybutyrate unexpectedly improves an individual's health.

In some implementations, the composition may be a natural composition. The combination of a natural R-beta-hydroxybutyrate with cannabidiol may provide a more natural composition that improves the health of an individual with dietary preferences for the consumption of natural products. The availability of a natural composition with natural R-beta-hydroxybutyrate (e.g., produced via bacterial fermentation in some implementations) with cannabidiol may provide benefits to a wider audience that may be excluded from other products due to dietary restrictions and/or preferences. In some implementations, other natural ingredients such as natural fatty acids such as coconut oil may be included in the composition. The natural composition may more readily utilized by the body and thus a lower amount of natural composition may be able to be utilized to achieve the same results, in some implementations.

In some implementations, the first composition may include at least approximately 5 mg of cannabidiol. The first composition may include less than approximately 1500 mg of cannabidiol. The first composition may include approximately 5 mg to approximately 300 mg of cannabidiol. In some implementations, the first composition may include approximately 10 mg to approximately 150 mg of cannabidiol.

The butyrate, beta-hydroxybutyrate and/or related compounds included in the first composition may include beta-hydroxybutyrate (e.g., R-beta-hydroxybutyrate, L-beta-hydroxybutyrate, and/or D,L-beta-hydroxybutyrate), such as beta-hydroxybutyrate salts and/or beta-hydroxybutyrate esters. In some implementations, beta-hydroxybutyrate may include beta-hydroxybutyrate bound to another compound (e.g., amino acids) and/or polymers of beta-hydroxybutyrate. For example, beta-hydroxybutyrate (e.g., R-beta-hydroxybutyrate, L-beta-hydroxybutyrate, and/or D,L-beta-hydroxybutyrate) may include beta-hydroxybutyrate salts, beta-hydroxybutyrate esters, beta-hydroxybutyrate sodium salt (e.g., sodium beta-hydroxybutyrate), beta-hydroxy butyrate potassium salt (e.g., potassium beta-hydroxybutyrate), beta-hydroxybutyrate calcium salt (e.g., calcium beta-hydroxybutyrate), beta-hydroxybutyrate magnesium salt (e.g., magnesium beta-hydroxybutyrate), beta-hydroxybutyrate lithium salt (e.g., lithium beta-hydroxybutyrate), sodium beta-hydroxybutyrate, arginine beta-hydroxybutyrate, lysine beta-hydroxybutyrate, histidine beta-hydroxybutyrate, ornithine beta-hydroxybutyrate, creatine beta-hydroxybutyrate, agmatine beta-hydroxybutyrate, or citrulline beta-hydroxybutyrate, other appropriate organic salts that include beta-hydroxybutyrate, and/or combinations thereof. In some implementations, the beta-hydroxybutyrate may include beta-hydroxybutyrate salts including (calcium, sodium, magnesium, potassium, zinc, selenium, chromium, other appropriate minerals, and/or combinations thereof). In some implementations, more than one type of beta-hydroxybutyrate salts may be utilized. For example, rather than utilizing 10 g of sodium beta-hydroxybutyrate, the composition may include approximately 5 grams of sodium beta-hydroxybutyrate, approximately 3 grams of calcium beta-hydroxybutyrate, and 2 grams of magnesium beta-hydroxybutyrate. The mixture of beta-hydroxybutyrate salts may reduce side effects from excess sodium, potassium, and/or magnesium. The use of three salts may have an unexpected result due to the ability of the body to tolerate greater amounts of beta-hydroxybutyrate salt due to the use of the three salt blend. In some implementations, more than three or less than three types of beta-hydroxybutyrate salts may be utilized in the composition. As another example, specific beta-hydroxybutyrate blends may be utilized based on the health of an individual. For example, for individuals with sodium sensitivity, a portion of the beta-hydroxybutyrate in the composition may be non-sodium beta-hydroxybutyrate (e.g., potassium beta-hydroxybutyrate, polymer of beta-hydroxybutyrate, etc.). In some implementations, the beta-hydroxybutyrate may be complexed and/or coupled to another compound (e.g., amino acid and/or berberine) and a beta-hydroxybutyrate salt may include a complex (e.g., chelate) that includes a mineral (e.g., calcium, zinc, etc.) and the beta-hydroxybutyrate compound coupled to another compound. The beta-hydroxybutyrate may include single isomer beta-hydroxybutyrate and/or polymer beta-hydroxybutyrate. For example, R-beta-hydroxybutyrate may include single isomer R-beta-hydroxybutyrate and/or polymer R-beta-hydroxybutyrate. In some implementations, beta-hydroxybutyrate may be administered with 1,3-butanediol, ethyl acetoacetate, ethyl beta-hydroxybutyrate. The beta-hydroxybutyrate may include a naturally formed beta-hydroxybutyrate, such as R-beta-hydroxybutyrate produced by microorganisms such as bacteria and/or fungi.

The beta-hydroxybutyrate may include racemic mixtures and/or individual isomers of betahydroxy-butyrate. In some implementations, one or more specific chiralities of beta-hydroxybutyrate may be utilized. For example, R-beta-hydroxybutyrate (also referred to as D-beta-hydroxybutyrate), S-beta-hydroxybutyrate (also referred to as L-beta-hydroxybutyrate), and/or mixtures (e.g., raecemic mixtures) thereof may be utilized. In some implementations, R-beta-hydroxybutyrate may be included in the first composition (e.g., a more purified form of R-beta-hydroxybutyrate rather than D,L-beta-hydroxybutyrate).

The first composition may include approximately 0.1 mg to approximately 50 g of butyrate and/or beta-hydroxybutyrate. In some implementations, less R-beta-hydroxybutyrate may be utilized than D,L-beta-hydroxybutyrate to provide the same administration result. For example, the first composition may include approximately 0.2 to approximately to approximately 20 mg of beta-hydroxybutyrate (e.g., R-beta-hydroxybutyrate). In some implementations, the first composition may include less than 2 mg of beta-hydroxybutyrate (e.g., R-beta-hydroxybutyrate). The first composition may include from approximately 0.5 mg to approximately 12 mg of beta-hydroxybutyrate (e.g., R-beta-hydroxybutyrate).

In some implementations, R-beta-hydroxybutyrate may be utilized rather than L-beta-hydroxybutyrate and/or D,L-beta-hydroxybutyrate. For example, the first composition may include R-beta-hydroxybutyrate and may include less than approximately 10 percent, less than approximately 5 percent, or less than approximately 1 percent L-beta-hydroxybutyrate. R-beta-hydroxybutyrate may have a greater bioavailability than other chiralities of beta-hydroxybutyrate. R-beta-hydroxybutyrate may have a greater impact on a health of an individual (e.g., due to decreased side effects; increase ketone levels, weight loss, mental acuity, fat loss, etc.) than L-beta-hydroxybutyrate and/or D,L-beta-hydroxybutyrate. In some implementations, R-beta-hydroxybutyrate may cause improvements in health not capable by L-beta-hydroxybutyrate and/or D,L-beta-hydroxybutyrate. R-beta-hydroxybutyrate may have less impurities due to manufacturing, such as less crotonic acid (e.g., which can be harmful to individuals), than other forms of beta-hydroxybutyrate (e.g., L-beta-hydroxybutyrate and/or D,L-beta-hydroxybutyrate). For example, the composition may include less than approximately 10%, less than approximately 5%, and/or less than approximately 2% crotonic acid. In some implementations, R-beta-hydroxybutyrate may be more capable of binding with other compounds (e.g., purine, lysine, potassium, and/or other amino acids; dihydroberberine; etc.) to deliver the beta-hydroxybutyrate to a human. Thus, R-beta-hydroxybutyrate (e.g., greater than 90 percent purity of R-beta-hydroxybutyrate and less than 10 percent L-beta-hydroxybutyrate) and/or mixtures with R-beta-hydroxybutyrate may be administered to humans. In some implementations, unexpectedly, a smaller amount of R-beta-hydroxybutyrate may be as pharmaceutically effective (e.g., in increasing and/or maintaining weight loss; in increasing and/or maintaining elevated ketone levels, etc.) or more pharmaceutically effective as D,L-beta-hydroxybutyrate (e.g., raecemic mixture of D- and L-beta-hydroxybutyrate). For example, approximately half an amount of R-beta-hydroxybutyrate may be administered to achieve the approximately the same efficacy as D,L-beta-hydroxybutyrate and/or L-beta-hydroxybutyrate. The R-beta-hydroxybutyrate may be more bioavailable than other chiralities of beta-hydroxybutyrate and thus allow a smaller effective amount than other chiralities. Thus, by utilizing R-beta-hydroxybutyrate, the administration amount of beta-hydroxybutyrate to be reduced (e.g., when compared to the administration amount of D,L-beta-hydroxybutyrate) while providing a pharmaceutically effective amount, such as (e.g., for weight loss and/or maintenance; for elevating and/or maintaining blood ketone levels). Reducing the amount of beta-hydroxybutyrate, when the beta-hydroxybutyrate is provided in salt form, may reduce a user's intake of the cation of the salt (e.g., sodium, potassium, etc.). Since intake of some of these cations in beta-hydroxybutyrate salts, such as sodium, potassium, magnesium, and calcium, in amounts greater than a predetermined recommended amount may cause health problems (e.g., organ damage, gastrointestinal problems, etc.), reducing the amount of beta-hydroxybutyrate salt by using R-beta-hydroxybutyrate may inhibit side effects and/or health problems associated salts combined with beta-hydroxybutyrate administration in users.

The benefits of the R-beta-hydroxybutyrate may be increased by a more than cumulative amount by administration of R-beta-hydroxybutyrate with cannabidiol.

The first composition may be administered on a regular and/or irregular schedule. The first composition may be administered up to 5 times a day in some implementations. The first composition may be administered in different forms throughout an administration schedule. For example, the first composition may be administered through beverages such as coffee and/or coffee supplements, teas, bone broth, etc. The first composition may be administered as a food and/or food supplement. The first composition may be administered as supplements in the form of tablets, capsules, etc.

Administration of the first composition may improve and/or maintain a health of an individual. For example, administration of the first composition that includes cannabidiol, butyrate, and/or beta-hydroxybutyrate may improve and/or maintain cognitive function. Cognitive function may decline with age, disease, and/or diet, and administration of the first composition may maintain cognitive function. Cognitive function may decline during periods of time (e.g., after meals, after working for a period of time, etc.), and administration of the first composition may improve and/or maintain cognitive function. Cognitive function in healthy adults may improve with the administration of the first composition. The Brain Derived Neurotrophic Factor (BDNF) is neural growth factor that is heavily involved in the growth, development, and preservation of neurons and thus impacts cognitive functioning, synaptic plasticity and memory. Both BHB and CBD may promote Bdnf release and expression, which may magnify Bdnf release. Thus, cognitive function and/or memory may be increased with administration of the first composition. Additionally, the administration of the first composition may reduce common side effects of keto diets, such as feelings of a mental fog.

Administration of the first composition may improve and/or maintain body composition. In fit individuals, maintenance of body composition may be facilitated. Administration of the first composition may reduce appetite, increase satiety, and/or improve body composition. Butyrate and/or beta-hydroxybutyrate may work with cannabidiol to increase ketone production and/or facilitate inducing and/or maintaining ketosis in an individual. Butyrate and/or beta-hydroxybutyrate may work with cannabidiol to lower available glucose and/or increase fat oxidation. Weight loss may and/or improved body composition may occur via administration of the first composition due to the increased weight loss (e.g., due to ketosis and/or reduced food intake) and/or fat oxidation.

Administration of the first composition may increase performance. Performance may be decreased by inflammation and/or pain. Thus, since administration of the first composition may decrease inflammation and/or pain, the first composition may increase performance. The cannabidiol and beta-hydroxybutyrate in the first composition may inhibit pro-inflammatory cytokines production. The specific cytokine suppressed may be different for cannabidiol and beta-hydroxybutyrate; however, the components of the first compound may not reduce each cytokine suppression but rather cause a greater suppression of cytokine than components individually (e.g., cannabidiol may inhibit T-regulatory cells and may suppress inflammatory responses from TNF-a, GM-CSF, IFN-Y, and/or IL-12; beta-hydroxybutyrate may reduces IL-1 and IL-18 production). In combination, cannabidiol and beta-hydroxybutyrate may have a greater effect on limiting the overall amount of pro-inflammatory cytokines, and thus, may increase muscle mobility and may reduce pain. This may result in overall increase in athletic performance. Additionally, since performance may include a mental factor, the increased cognitive function provided with the administration of the first composition may further increase performance as well.

Administration of the first composition may decrease immune function. When cannabidiol acts on CB2 receptors in the immune system, a cascade is triggered that leads to immunosuppression via marked apoptosis of dendritic and T-cells. This is a novel approach to treating inflammatory disorders, primarily autoimmune diseases caused by reactive T-cells. Beta-hydroxybutyrate has the unique ability to inhibit the NLRP3 inflammasome, which is responsible for the cleavage and activation to IL-1 and IL-18. Both pro-inflammatory cytokines are responsible for induction of inflammation, however IL-1 also plays a vital role in the activation of T-cells. When used in combination, cannabidiol and beta-hydroxybutyrate may have a greater effect on eliminating T-lymphocytes, and thus reducing inflammation and/or autoimmune destruction. Although immune system suppression may sound like a harmful effect, the mechanisms by which this specific immunosuppression occurs causes the modulation in immune response dominance from TH1 to TH2, whereas TH2 are T helper cells and do not widely contribute to autoimmune destruction like TH1 cytotoxic T cells. Thus, administration of the first composition may be beneficial to traditional autoimmune and inflammatory conditions. In some implementations, the amalgamation of cannabidiol and beta-hydroxybutyrate (e.g., due to a delay insulitis and/or improve blood glucose control) may inhibit and/or prolong the onset of type I diabetes (e.g., through the elimination of destructive autoimmune T-cells that would otherwise destroy beta cells of the pancreas).

Administration of the first composition may increase glucose control. Beta-hydroxybutyrate, BHB, may lower blood glucose and/or improve control by limiting spikes in these levels and cannabidiol may inhibit insulin resistance. Thus, administration of the first composition may increase insulin response, lowering blood glucose levels, and facilitate control of blood glucose levels. These effects may be significantly magnified when administering beta-hydroxybutyrate and cannabidiol together (e.g., both may lower blood glucose through the utilization of different mechanisms). In some implementations, berberine and/or dihydroberberine may include in the composition to control glucose levels. While dihydroberberine has an unexpectedly manage glucose levels, as outlined in U.S. patent application Ser. No. 15/491,933, which is incorporated by reference herein to the extent that it does not contradict the teachings herein, the use of dihydroberberine with beta-hydroxybutyrate and cannabidiol increases the glucose tolerance provided (e.g., in terms of level, duration, etc.).

Administration of the first composition may improve health in individuals with substance abuse problems. In some implementations, administration of the first composition may decrease withdrawal symptoms and/or probability of relapse. CB1 receptor activation by cannabidiol plays a substantial role in reducing mesolimbic pathway stimulation such that drug-seeking behaviors may be decreased in individuals suffering from substance abuse disorders when administered the first composition. Increased ketone levels from administration of the first composition may improve withdrawal symptoms during the detoxification process, such that relapse rates were substantially decreased. Thus, substance abuse disorder and/or chronic drug addiction may include administration of the first composition (e.g., to reduce cravings and/or other symptoms of withdrawal).

Administration of the first composition may improve the health of people with neurodegenerative diseases. For example, symptoms of the neurodegenerative disease may be decreased. Deficiency in bioenergetics due to mitochondrial deficiency is a common mechanism implied in neurogenerative diseases. The first composition may modulate glucose metabolism in such a way that mitochondrial bioenergetics are enhanced and/or overall energy utilization is improved. Cannabidiol may stimulate the pentose-phosphate pathway through glucose-6-phosphate dehydrogenase activation and thus leads to increased NADPH production. NADPH is not only a key component of in DNA synthesis, but also functions as an anti-oxidant. Such antioxidants may eliminate free radicals and/or prevent oxidative damage, thereby inhibiting neurodegenerative disease and/or progression of neurodegenerative disease. Ketone bodies, such as beta-hydroxybutyrate, may more readily cross the blood-brain-barrier, bypass complex I in the electron transport chain, and increase mitochondrial biogenesis. This may cause increased neuronal energy utilization and/or decreased oxidative damage. Cannabidiol and beta-hydroxybutyrate may operate in a complementary manner rather than competitive. Thus, the first composition may treat neurodegenerative disease through improved energy utilization and/or inhibit incidence due to amplified antioxidant effects.

In various implementations, the first composition may one or more other compounds. For example, the first composition may include amino acid. The amino acid may be administered with the first composition and/or coupled with the beta-hydroxybutyrate, such as R-beta-hydroxybutyrate. For example, beta-hydroxybutyrate may be coupled to (e.g., chemically bonded to) amino acids, such as leucine, lysine, arginine, histidine, ornithine, creatine, agmatine, citrulline and/or combinations thereof. In some implementations, R-beta-hydroxybutyrate may be utilized rather than other chiralities since R-beta-hydroxybutyrate may be more easily bound to leucine, purine, lysine, and/or other amino acids. Administration of beta-hydroxybutyrate that is coupled to an amino acid may reduce the intake of cations associated with beta-hydroxybutyrate salts (e.g., which may inhibit side effects associated with administration) and/or allow administration of another compound that has health benefits (e.g., administration of some amino acid may promote smooth muscle growth and/or cell repair). In some implementations, approximately 0.5 g to approximately 10 g of amino acid may be administered with a beta-hydroxybutyrate. For example, less than approximately 50 g of R-beta-hydroxybutyrate and less than approximately 60 mg of an amino acid, such as leucine, may be administered daily. In some implementations, approximately 0.5 g to approximately 2 g of an amino acid, such as leucine, may be administered with a beta-hydroxybutyrate. For example, approximately the composition administered may include approximately 0.1 to approximately 7 g R-beta-hydroxybutyrate and approximately 1-3 g of leucine. The R-beta-hydroxybutyrate and the leucine may be a mixture; administered separately and proximate in timing; a complex, and/or administered in any other appropriate manner.

In some implementations, the composition may include R-beta-hydroxybutyrate salt and beta-hydroxybutyrate—amino acid complex (e.g., beta-hydroxybutyrate bound to amino acid, such as R-beta-hydroxybutyrate—leucine complex). For example, an individual may be administered a first weight amount of sodium beta-hydroxybutyrate and a second weight amount of beta-hydroxybutyrate amino-acid complex. The first amount and the second amount may be different or the same.

In some implementations, the beta-hydroxybutyrate composition of the first composition may include beta-hydroxybutyrate salt(s) and beta-hydroxybutyrate ester(s). For example, an individual may be administered a first weight amount of sodium beta-hydroxybutyrate and a second weight amount of beta-hydroxybutyrate ester. The first amount and the second amount may be different or the same. The beta-hydroxybutyrate salt and the beta-hydroxybutyrate ester may be a bound complex, a mixture of compounds, and/or separately administered approximately concurrently. In some implementations, the beta-hydroxybutyrate ester may be in powdered form (e.g., plated beta-hydroxybutyrate ester), liquid and/or gel form. The combination of beta-hydroxybutyrate salt and beta-hydroxybutyrate ester during administration may allow less salt to be utilized while producing a result (e.g., weight maintenance and/or loss; enhanced and/or maintained ketosis; elevated blood ketone levels; blood glucose reduction and/or maintenance; increase in energy; increase in mood; increase in performance; and/or increase in cognitive function). In some implementations, elevated ketone levels (e.g., elevated blood ketone levels) may increase energy, mood, performance, and/or cognitive function in users. For example, the administration of the first amount of beta-hydroxybutyrate salt may cause a first level of blood ketone level, which may be maintained by processing of the second amount of the beta-hydroxybutyrate ester (e.g., as the body of the individual processes the beta-hydroxybutyrate ester the level of beta-hydroxybutyrate in the blood, and thus blood ketone level, may also increase over time to enhance and/or maintain the initial elevation caused by of the administered beta-hydroxybutyrate salt.). For example, a ratio of beta-hydroxybutyrate to beta-hydroxybutyrate ester may be approximately 1 beta-hydroxybutyrate salt: approximately 1 beta-hydroxybutyrate ester to approximately 1 beta-hydroxybutyrate salt: approximately 20 beta-hydroxybutyrate ester. The ratio of beta-hydroxybutyrate to beta-hydroxybutyrate ester may be approximately 20 beta-hydroxybutyrate salt: approximately 1 beta-hydroxybutyrate ester to approximately 1 beta-hydroxybutyrate salt: approximately 20 beta-hydroxybutyrate ester. In some implementations, a ratio of beta-hydroxybutyrate to beta-hydroxybutyrate ester may be approximately 1 beta-hydroxybutyrate salt: approximately 1 beta-hydroxybutyrate ester to approximately 1 beta-hydroxybutyrate salt: approximately 5 beta-hydroxybutyrate ester.

Related compounds of beta-hydroxybutyrate may included in the first composition, such as derivatives of beta-hydroxybutyrate, include esters of (R)-3-hydroxybutyrate and oligomers of (R)-3-hydroxybutyrate. For example, beta-hydroxybutyrate esters derived from alcohols, such as altrose, arabinose, dextrose, erythrose, fructose, galactose, glucose, glycerol, gulose, idose, lactose, lyxose, mannose, ribitol, ribose, ribulose, sucrose, talose, threose, xylitol, xylose, galactosamine, glucosamine, mannosamine, N-acetylglucosamine, mannitol, sorbitol, threitol, (S)-1,2-propanediol and/or (R)-1,3-butanediol. In some implementations, a derivative of the beta-hydroxybutyrate may include structures of (R)-3-hydroxybutyric acid and an exemplary ester thereof (a glycerol monoester). The R chirality of the derivatives may be selected for inclusion in the composition in some implementations (e.g., to deliver R-beta-hydroxybutyrate with the administration of the compound).

In some implementations, the first composition may include additional compounds may or may not be capable of independently increasing ketone levels, maintaining ketone levels, inducing ketosis, and/or maintaining ketosis. For example, additional compounds capable of independently increasing blood ketone levels may include short chain fatty acids (e.g., fatty acid with between 2 carbons than 6 carbons), short chain triglycerides (e.g., triglycerides with less than 6 carbons), medium chain fatty acids (e.g., fatty acid with 6-12 carbons), medium chain triglycerides (e.g., triglycerides with 7-12 carbons), long chain fatty acids (e.g., fatty acids with more than 12 carbons), long chain triglycerides (e.g., triglycerides with more than 12 carbons), and/or combinations thereof. In some implementations, short chain fatty acids and/or triglycerides may include acetate, propionate, and/or butyrate. Medium chain fatty acids and/or triglycerides may include lauric acid and/or coconut oil, coconut milk powder, fractionated coconut oil, isolated hexanoic acid, isolated octanoic acid, isolated decanoic acid, ethoxylated triglyceride, triglyceride derivatives thereof, aldehyde triglyceride derivatives thereof, monoglyceride derivatives thereof, diglyceride derivatives thereof, triglyceride derivatives thereof, and/or alkyl esters thereof. Long chain fatty acids and/or triglycerides may include dairy products and/or palm oil. In some implementations, a compound including R-beta-hydroxybutyrate and an additional compound that is independently capable of increasing ketone levels may increase ketone levels greater than merely the capability of each component individually (e.g., greater than an additive increase).

For example, a pharmaceutically effective amount of one or more short chain fatty acids and/or one or more short chain triglycerides (e.g., butyric acid and/or butyrate) may be administered with a pharmaceutically effective amount of beta-hydroxybutyrate. In some implementations, approximately 1 g to approximately 10 g of beta-hydroxybutyrate and approximately 0.1 g to approximately 50 g of short chain fatty acid and/or triglyceride may be administered from once a day to approximately 5 times a day. In some implementations, approximately 1 g to approximately 3 g of beta-hydroxybutyrate and approximately 1 g of short chain fatty acid and/or triglyceride may be administered from once a day to approximately 5 times a day. In some implementations, the short chain fatty acid and/or triglyceride may include butyrate or derivatives of butyrate. Butyrate and/or derivatives of butyrate may be administered with and/or without beta-hydroxybutyrate to manage metabolic conditions, such as ketosis, and/or for other appropriate therapeutic purposes. Administered butyrate may be converted to beta-hydroxybutyrate in humans, and thus may increase the amount of beta-hydroxybutyrate delivered to the user. In some implementations, administration of butyrate and beta-hydroxybutyrate may promote hGH synthesis, improve basal and GHRH-induced hGH-secretion, increase muscle fiber cross-sectional area, inhibit intramuscular fat accumulation; reduce fat mass in a user; improve glucose metabolism; increase markers of mitochondrial biogenesis in skeletal muscle and/or whole-body oxygen consumption; reduced markers of oxidative stress and apoptosis and altered antioxidant enzyme activity; cause butyrate enhanced intracellular free cytosolic calcium levels (e.g., by acting through GPR41 and 43); increase beta-hydroxybutyrate levels; and/or support barrier function(s) in the gut and/or reduce inflammation associated with ulcerative colitis. Since butyrate is processed by the body to provide beta-hydroxybutyrate, the delivery of beta-hydroxybutyrate via the butyrate may supplement the directly administered beta-hydroxybutyrate to maintain a level of beta-hydroxybutyrate in the blood (e.g., to promote ketosis, weight loss and/or management, etc.).

Butyrate and/or butyric acid may not be palatable to individuals (e.g., since the odor and taste are often compared to vomit). Thus, in some implementations, butyrate and/or beta-hydroxybutyrate (e.g., R-beta-hydroxybutyrate) may be processed to reduce organoleptic reactions. For example, the butyrate and/or beta-hydroxybutyrate (e.g., R-beta-hydroxybutyrate) may be encapsulated, microemulsion, liposomes, agglomeration, masking/flavoring technologies, and/or otherwise processed as appropriate to reduce organoleptic reactions from individuals administered the described composition(s). In some implementations, microencapsulated butyrate, beta-hydroxybutyrate, and/or butyric acid may be utilized (e.g., in combination with beta-hydroxybutyrate). Using microencapsulated butyrate, beta-hydroxybutyrate, and/or butyric acid (e.g., when compared with using unencapsulated forms) may increase individual satisfaction and/or compliance with an administration schedule since odor from the butyrate and/or butyric acid may be reduced and/or removed. The microencapsulated butyrate, beta-hydroxybutyrate, and/or butyric acid may be a free flowing granular powder; dispersible in water; stable in acidic water solution for approximately 30 minutes; allow controlled release in stomach and/or small intestines; inhibit glucose response (e.g., to any added materials); and/or allow delivery of a high butyrate content (e.g., around 70%).

In some implementations, a pharmaceutically effective amount of butyrate may be administered via triglyceride tributyrin (e.g., glyceryl tributyrate or tributyrin). The butyrate via triglyceride tributyrin may be administered separately and/or in conjunction with one or more of the other described compounds (e.g., beta-hydroxybutyrate, fatty acids and/or esters, etc.). For example, up to approximately 200 mg/kg of the individual may be administered (e.g., up to 3 times daily). Administration of the tributyrin may allow a delayed release of butyrate to the body as the tributyrin is processed by the body of the individual. The tributyrin may be unencapsulated and/or encapsulated (e.g., microencapsulated).

In some implementations, administration of beta-hydroxybutyrate and a short chain compound (e.g., short chain fatty acid and/or short chain triglyceride) may unexpectedly increase beta-hydroxybutyrate concentrations in the blood more than the administration of similar amounts of beta-hydroxybutyrate and medium chain compounds (e.g., short chain fatty acid and/or short chain triglyceride) and/or may increase beta-hydroxybutyrate concentrations in the blood more than each component individually.

In some implementations, a pharmaceutically effective amount of beta-hydroxybutyrate and a pharmaceutically effective amount of cannabidiol may be administered with a pharmaceutically effective amount of long chain fatty acid and/or triglyceride. For example, 0.1-50 g of beta-hydroxybutyrate and 0.1 to 50 g of long chain fatty acid may be administered to an individual between 1-5 times a day. In some implementations, approximately 1 g to approximately 3 g of beta-hydroxybutyrate and approximately 1 g of long chain fatty acid and/or triglyceride may be administered from once a day to approximately 5 times a day.

In some implementations, the first composition may include short chain compound(s) (e.g., fatty acids and/or triglycerides, butyrate), and/or medium chain compound(s) (e.g., fatty acids and/or triglycerides) may be administered approximately simultaneously and/or sequentially to an individual. For example, approximately 0.1 g to approximately 50 g short chain triglyceride, and approximately 0.1 g to approximately 50 g medium chain fatty acid such as lauric acid and/or coconut oil may be administered between 1-5 times a day. In some implementations, approximately 1 g of short chain fatty acid and/or triglyceride and/or approximately 1 g of medium chain fatty acid and/or triglyceride may be administered from once a day to approximately 5 times a day.

In some implementations, other compounds, such as compounds capable of independently decreasing glucose levels, may be included in the first composition, such as berberine and/or associated metabolites (e.g., dihydroberberine and/or tetrahydroberberine). U.S. patent application Ser. No. 15/491,933 entitled "ADMINISTRATION OF DIHYDROBERBERINE" to Lowery et al, filed Apr. 19, 2017 and U.S. Provisional Patent Application No. 62/324,794, entitled "ADMINISTRATION OF DIHYDROBERBERINE" to Lowery et al, filed Apr. 19, 2016, describe dihydroberberine administration with ketone sensitizers such as beta-hydroxybutyrate, and is hereby fully incorporated herein. In some implementations, the first composition may include other compounds described herein as a ketone sensitizer with the dihydroberberine.

In some implementations, directly administering beta-hydroxybutyrate of the first composition with another compound that is processed to deliver beta-hydroxybutyrate (e.g., beta-hydroxybutyrate ester, beta-hydroxybutyrate polymer, butyrate, other appropriate compounds, and/or combinations thereof) over time may allow a first level of beta-hydroxybutyrate in the blood to be maintained over a period of time. For example, since the directly administered beta-hydroxybutyrate may elevate blood beta-hydroxybutyrate levels to a first concentration and this concentration may be approximately maintained over a period of time by providing additional beta-hydroxybutyrate via another compound administered approximately concurrently (e.g., short chain fatty acid and/or triglyceride, beta-hydroxybutyrate ester, beta-hydroxybutyrate polymer, beta-hydroxybutyrate amino acid complex, etc.).

In some implementations, the first composition may include one or more other compounds such as, but are not limited to amino acids, amino acid metabolites, vitamins, minerals, coconut milk powder, flavorings, colorings, binders, electrolytes, tetrahydrobiopeterin, nucleic acids, alpha-ketoglutaric acid, alpha lipoic acid, nutritional co-factors, beta-methyl-beta-hydroxybutyrate, arginine alpha-ketoglutarate, R-alpha lipoic acid, thiamine, NAD+, NADH, riboflavin, FAD+, FADH, riboflavin-5-phosphate, niacin, nicotinic acid, niacinamide, inositol hexanicotinate, pyridoxine, pyridoxal, pyridoxamine, ascorbic acid and ascorbate salts, citric acid, malic acid, sodium benzoate, Pyridoxal-5-Phosphate, methylcobalamin, cyanocobalamin, adenosylcobalamin, hydroxycobalamin, pantothenic acid, pantetheine, potassium sorbate, acesulfame K, aspartame, sucralose, *stevia*, monk fruit extract, allulose, prebiotic fibers, XOS, GOS, MOS, IMO, LOS, xanthan gum and other organic gums/thickeners/suspension agents, and combinations thereof.

In various implementations, administration of a composition that includes beta-hydroxybutyrate may improve the health of an individual. R-beta-hydroxybutyrate may be capable of providing a greater impact on the health of an individual than D,L-beta-hydroxybutyrate and/or L-beta-hydroxybutyrate. Although previously unknown, L-beta-hydroxybutyrate may decrease the effectiveness of R-beta-hydroxybutyrate with respect to at least a portion of the impact on health. With respect to some impacts on health, L-beta-hydroxybutyrate may have no impact on health. In some implementations, even double the amount of D,L-beta-hydroxybutyrate may not achieve some of the same results (e.g., in health improvement) as R-beta-hydroxybutyrate. Thus, unexpectedly administration of D,L-beta-hydroxybutyrate rather than R-beta-hydroxybutyrate may not have the same impact on health and/or have less of an impact on health of an individual. For example, administration of a composition that includes R-beta-hydroxybutyrate (e.g., and/or other compounds) may improve and/or maintain an individual's health.

Administration of R-beta-hydroxybutyrate as described may increase lifespan in individuals following a dietary plan (e.g., standard American low-fat, ketogenic, Paleo, Mediterranean, etc.) and/or not following a dietary plan. For example, approximately 10 g of R-beta-hydroxybutyrate to approximately 30 g R-beta-hydroxybutyrate may be administered to increase lifespan. In some implementations, other appropriate amounts of R-beta-hydroxybutyrate may be included in the composition.

In some implementations, administration of R-beta-hydroxybutyrate may treat and/or lessen the impact of symptoms of disease(s) and/or disorders, such as diseases that impact cognitive function. Administration of R-beta-hydroxybutyrate may increase motor function in individuals with Parkinson's disease. For example, approximately 5 g of R-beta-hydroxybutyrate to approximately 15 g R-beta-hydroxybutyrate may be administered to increase motor function. In some implementations, other appropriate amounts of R-beta-hydroxybutyrate may be included in the composition.

Administration of R-beta-hydroxybutyrate may increase fat loss. Unlike with conventional diets, in which weight loss often comes from decreases in water retention and/or muscle mass, administration of R-beta-hydroxybutyrate may cause decreases in fat loss (see for example, FIG. 5B). In addition, administration of R-beta-hydroxybutyrate may decrease levels of LPL in the body, and thus reduce or inhibit fat storage and/or encourage existing fat storage utilization by the body. For example, approximately 1 g of R-beta-hydroxybutyrate to approximately 20 g R-beta-hydroxybutyrate may be administered to cause fat loss and/or reduce fat storage. In some implementations, other appropriate amounts of R-beta-hydroxybutyrate may be included in the composition. Administration of R-beta-hydroxybutyrate may allow fat loss greater than 5 kg while maintaining lean mass. In some implementations, the administration of R-beta-hydroxybutyrate increases the amount of fat used as fuel.

In some implementations, administration of R-beta-hydroxybutyrate may improve and/or maintain health markers such as C-reactive protein and/or fasting glucose. Administration of R-beta-hydroxybutyrate may decrease inflammation (e.g., as shown by C-reactive protein levels). Administration of R-beta-hydroxybutyrate may decrease fasting glucose. For example, approximately 3 g of R-beta-hydroxybutyrate to approximately 20 g R-beta-hydroxybutyrate may be administered to cause a reduction in and/or maintain a low fasting glucose. In some implementations, other appropriate amounts of R-beta-hydroxybutyrate may be included in the composition. In some implementations, R-beta-hydroxybutyrate may be administered with one or more other compounds to decrease glucose levels and/or sensitivity. For example, administration of a composition of R-beta-hydroxybutyrate and a berberine, such as dihydroberberine, may cause reduce and/or maintain low fasting glucose. Administration of a composition of R-beta-hydroxybutyrate and a berberine, such as dihydroberberine, may cause reduce and/or maintain low glucose levels. In some implementations, less than approximately 15 g of R-beta-hydroxybutyrate may be administered with less than approximately 600 mg of dihydroberberine.

Administration of R-beta-hydroxybutyrate may decrease ketone levels (see e.g., FIGS. 11A and 11B). Decreasing blood ketone levels may increase weight loss, maintain weight loss, improve performance, increase mental acuity, and/or have other health improvement and health maintenance features. For example, even at levels less than 10 g (e.g., approximately 5 g), administration of R-beta-hydroxybutyrate may decrease ketone levels while L-R-beta-hydroxybutyrate does not, and D,L-beta-hydroxybutyrate does not to the same extent. R-beta-hydroxybutyrate may increase blood ketone levels 5 times as much as similar administration amounts of D,L-beta-hydroxybutyrate. By being able to decrease an amount of R-beta-hydroxybutyrate (e.g., when compared with administering D,L-beta-hydroxybutyrate) administered and achieve the same results, a decrease in an amount cation (e.g., sodium, potassium, etc.) may also be administered. Since some individuals may prefer and/or may not tolerate higher dosages of the cations of the R-beta-hydroxybutyrate salt, utilizing R-beta-hydroxybutyrate may allow administration to more people, increase user satisfaction, and/or decrease side effects (e.g., associated with additional consumption of these cations). In some implementations, approximately 0.1 g of R-beta-hydroxybutyrate to approximately 10 g R-beta-hydroxybutyrate may be administered to increase blood ketone levels. Approximately 0.5 g of R-beta-hydroxybutyrate to approximately 3 g R-beta-hydroxybutyrate may be administered to maintain blood ketone levels. In some implementations, other appropriate amounts of R-beta-hydroxybutyrate may be included in the composition.

Administration of R-beta-hydroxybutyrate may increase performance and decrease perceived exertion (e.g., as opposed to when administered D,L-beta-hydroxybutyrate). For example, approximately 3 g of R-beta-hydroxybutyrate to approximately 15 g R-beta-hydroxybutyrate may be administered to increase performance and/or decrease perceived exertion. In some implementations, other appropriate amounts of R-beta-hydroxybutyrate may be included in the composition.

In various implementations, oral administration of R-beta-hydroxybutyrate may increase muscle protein synthesis while D,L-beta-hydroxybutyrate does not increase muscle protein synthesis. For example, approximately 10 g of R-beta-hydroxybutyrate to approximately 30 g R-beta-hydroxybutyrate may be administered to increase muscle protein synthesis. In some implementations, other appropriate amounts of R-beta-hydroxybutyrate may be included in the composition.

Figure 13A:
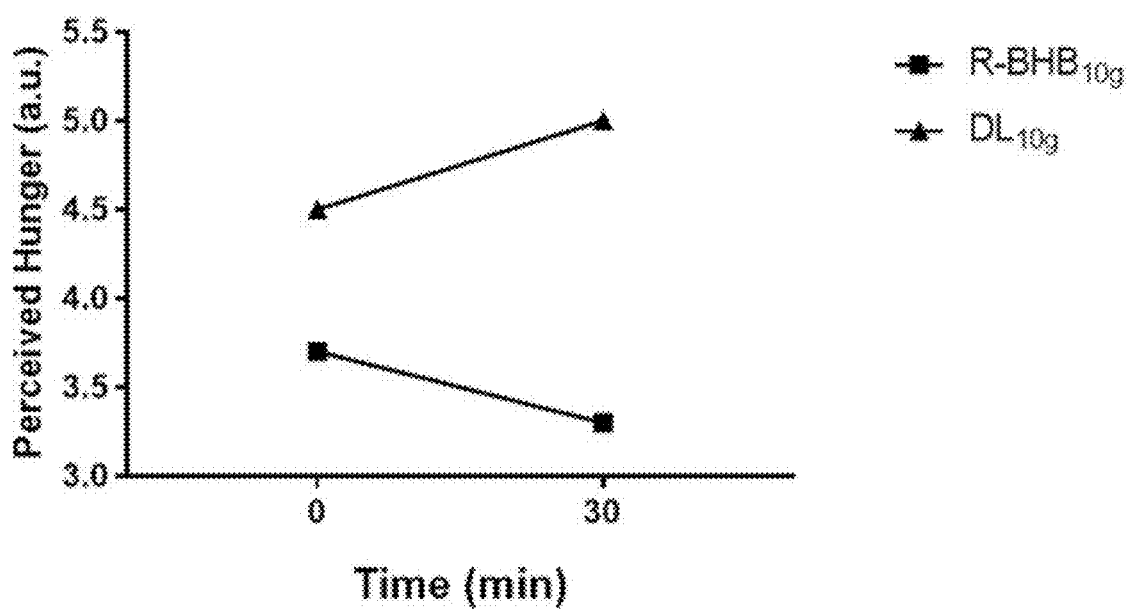
FIG. 13A illustrates a chart illustrating perceived hunger following an implementation of an example administration protocol.
Figure 13B:
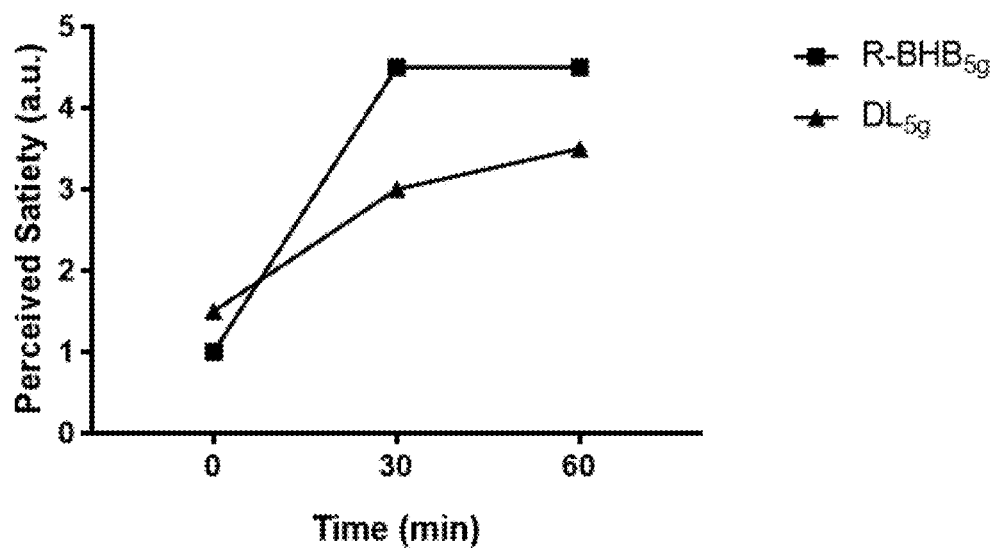
FIG. 13B illustrates a chart illustrating perceived satiety following an implementation of an example administration protocol.

In some implementations, the administration of R-beta-hydroxybutyrate, unlike D,L-beta-hydroxybutyrate may decrease perceived hunger and/or increase satiety) which may inhibit overeating and thus promote weight loss (see e.g., FIGS. 13A and 13B). In some implementations, the administration of R-beta-hydroxybutyrate, unlike D,L-beta-hydroxybutyrate may increased perceived energy (see e.g., FIG. 13C).

In some implementations, administration of R-beta-hydroxybutyrate increased mental acuity. For example, approximately 0.1 g of R-beta-hydroxybutyrate to approximately 10 g R-beta-hydroxybutyrate may be administered to increase mental acuity. In some implementations, other appropriate amounts of R-beta-hydroxybutyrate may be included in the composition.

In some implementations, the administration of R-beta-hydroxybutyrate may be supplemented with other forms of beta-hydroxybutyrate, butyric acid, and/or butyrate.

In some implementations, the composition administered may include R-beta-hydroxybutyrate. The amount of R-beta-hydroxybutyrate included in the composition may be selected to obtain a result (e.g., induce ketosis; maintain ketosis; increase ketone levels, mental acuity, strength, etc.) upon administration (e.g., a pharmaceutically effective amount may be administered at a dosage and/or over a predetermined time period). In some implementations, the dosage and/or frequency of dosage may vary over time (e.g., initial vs. a lower dosage for maintenance, vary based on time of day, vary based on whether taken with or without a meal, etc.).

The R-beta-hydroxybutyrate in the composition may include any appropriate and/or appropriate number of forms, such as salts, derivatives (e.g., esters), polymers, and/or complexes with other compounds. For example, the composition may include R-beta-hydroxybutyrate salt (e.g., sodium R-beta-hydroxybutyrate, magnesium R-beta-hydroxybutyrate, and/or potassium R-beta-hydroxybutyrate) and/or another form of R-beta-hydroxybutyrate (e.g., ester, polymer, complex, etc.). In some implementations, the composition may include an ester of R-beta-hydroxybutyrate. The composition may include an amino acid (e.g., separate and/or complexed with R-beta-hydroxybutyrate), such as leucine. The use of non-salt base R-beta-hydroxybutyrate may increase user satisfaction (e.g., by reducing the cation, such as sodium and/or potassium, load due to ingestion of the composition; by decreasing side effects; etc.), increase the applicability of the administration (e.g., since users sensitive to the cations of the R-beta-hydroxybutyrate salts may be less sensitive to the non-salt and/or lower salt plus non-salt forms of the composition). The administration of the composition may increase blood ketone levels, induce ketosis, maintain blood ketone levels, maintain ketosis, increase health, increase strength, increase mental acuity, etc. In some implementations, a first composition that includes R-beta-hydroxybutyrate salt may be administered to cause a first impact (e.g., induce ketosis, quickly increase mental acuity, quickly increase strength, etc.) and a second composition that includes non-salts R-beta-hydroxybutyrate (e.g., esters, polymers, complexes, etc.) and/or lower levels of R-beta-hydroxybutyrate salt may be utilized to cause a second impact (e.g., maintain ketosis, maintain mental acuity, maintain increased strength, etc.).

In some implementations, the form(s) of R-beta-hydroxybutyrate included in the composition may be selected based on the delivery form. For example, in some forms of food products the composition may include R-beta-hydroxybutyrate polymer (e.g., due to taste since increased cations like sodium may decrease palatability; due to nutrition since increased cations such as sodium may decrease nutrition; due to mixability, etc.). As another example, the composition may include R-beta-hydroxybutyrate salts or other forms (e.g., microencapsulated) to provide quick dissolve powders.

In various implementations, a composition may include R-beta-hydroxybutyrate. The R-beta-hydroxybutyrate may be in any appropriate form (e.g., salt, ester, polymer, complex, derivatives thereof, and/or combinations thereof). The composition may include one or more additional compositions. Additional composition(s) may be capable of independently increasing blood ketone levels (e.g., fatty acids or esters, berberine or berberine metabolites such as dihydroberberine, etc.). Additional composition(s) may be capable of independently decreasing blood glucose levels (e.g., berberine or berberine metabolites such as dihydroberberine). In some implementations, additional compounds may not be capable of independently increasing blood ketone levels and/or decreasing blood glucose levels (e.g., additives, flavorings, colorings, minerals, vitamins, binders, anti-caking agents, etc.). The composition may be administered in an effective amount to cause a predetermined health impact (e.g., predetermined level of ketosis, blood ketone level, mental acuity, strength increase, perceived energy, fat loss, weight loss, etc.). The composition may be administered to an individual in a predetermined amount and/or different amounts over an administration schedule. In some implementations, once a first criterion is satisfied (e.g., period of time, number of doses, predetermined health impact), the dosage amount may be altered. For example, first dose(s) of the composition may be administered to cause a predetermined health impact and additional lower dose(s) of the composition may be administered to maintain the predetermined health impact (e.g., caused in part by the first doses).

The composition may be administered in any appropriate delivery form (e.g., tablet; capsule; food products such as powdered products that can be mixed into food, mixed into beverages, and/or consumed directly; beverage product; etc.). The composition may be administered according to any appropriate schedule (e.g., periodic dosages, dosages as user desires, etc.). The administration schedule may inhibit administration that elevates blood ketone levels too high, decreases blood glucose levels too low, and/or causes an individual to consume a dosage that substantially elevates the risk of adverse and/or side effects, in some implementations.

In some implementations, the composition may include a long acting component and/or be long-acting. For example, since the body digests polymers and/or esters of beta-hydroxybutyrate (e.g., R-beta-hydroxybutyrate), the delivery of R-beta-hydroxybutyrate may be slower than a digestion of a beta-hydroxybutyrate salt (e.g., R-beta-hydroxybutyrate salt). In some implementations, the composition may include a R-beta-hydroxybutyrate and a long acting R-beta-hydroxybutyrate form (e.g., polymer, ester, coated and/or processed form to provide slow release). In some implementations, a first dose(s) may include at least one non-long acting form of beta-hydroxybutyrate and a second dose(s) may include at least one long-acting form of beta-hydroxybutyrate. The first dose(s) may be administered to cause a predetermined health impact and the second dose(s) may be administered to maintain the caused predetermined health impact. In some implementations, users may select the appropriate dose based on user preference and/or properties (e.g., a user on a ketogenic diet may chose the second dose since the user may already be in ketosis).

In various implementations, a composition for weight loss or weight management of an individual may include approximately 0.2 g to approximately 10 g of beta-hydroxybutyrate and at least approximately 5 mg of cannabidiol.

Implementations may include one or more of the following features. The amount of cannabidiol may include less than approximately 300 mg of cannabidiol. The beta-hydroxybutyrate may include approximately 95 weight percent to approximately 100 weight percent of R-beta-hydroxybutyrate and less than approximately 5 weight percent of L-beta-hydroxybutyrate. The beta-hydroxybutyrate may include a beta-hydroxybutyrate salt. The beta-hydroxybutyrate may include a beta-hydroxybutyrate salt and a polymer of beta-hydroxybutyrate. The beta-hydroxybutyrate may include a beta-hydroxybutyrate salt and an ester of beta-hydroxybutyrate. The combination of the beta-hydroxybutyrate salt along with the polymer or ester of beta-hydroxybutyrate and cannabidiol may quickly increase ketone levels and the polymer of beta-hydroxybutyrate and cannabidiol may provide a more sustained response (e.g., which may require fewer dosages and/or lower dosages). The combination of being able to quickly increase ketone levels to start fat burning while maintaining ketone levels with the polymer or ester of beta-hydroxybutyrate may provide a greater weight loss and/or maintenance impact than the impact of each component individually. The composition may include a fatty acid or ester thereof (e.g., short chain, long chain, and/or medium chain fatty acids or esters thereof). The composition may include approximately 0.5 g to approximately 10 g of amino acid. The addition of an amino acid such as leucine may increase the impact of the other components greater than expected to provide greater performance, weight loss, and/or appetite suppression. The composition may include at least one of berberine or dihydroberberine. The composition may be administered in encapsulated or in a powdered form. The composition may be administered as a food, drink, capsule, food additive, drink additive, powder, etc.

In various implementations, the composition may be administered to cause weight loss and/or to allow weight maintenance in an individual.

In various implementations, composition for improving or maintaining glucose levels may include approximately 0.2 g to approximately 10 g of beta-hydroxybutyrate (e.g., a beta-hydroxybutyrate salt) and approximately 5 mg to approximately 300 mg of cannabidiol.

Implementations may include one or more of the following features. The amount of cannabidiol may include less than approximately 300 mg of cannabidiol. The beta-hydroxybutyrate may include approximately 95 weight percent to approximately 100 weight percent of R-beta-hydroxybutyrate and less than approximately 5 weight percent of L-beta-hydroxybutyrate. The beta-hydroxybutyrate may include a beta-hydroxybutyrate salt. The beta-hydroxybutyrate may include a beta-hydroxybutyrate salt and a polymer of beta-hydroxybutyrate. The beta-hydroxybutyrate may include a beta-hydroxybutyrate salt and an ester of beta-hydroxybutyrate. The combination of the beta-hydroxybutyrate salt along with the polymer or ester of beta-hydroxybutyrate and cannabidiol may quickly increase ketone levels and the polymer of beta-hydroxybutyrate and cannabidiol may provide a more sustained response (e.g., which may require fewer dosages and/or lower dosages). The combination of being able to quickly increase ketone levels to start fat burning while maintaining ketone levels with the polymer or ester of beta-hydroxybutyrate may provide a greater blood glucose maintenance impact than the impact of each component individually. The composition may include a fatty acid or ester thereof (e.g., short chain, long chain, and/or medium chain fatty acids or esters thereof). The composition may include approximately 0.5 g to approximately 10 g of amino acid. The addition of an amino acid such as leucine may increase the impact of the other components greater than expected to provide greater glucose control and/or appetite suppression. The composition may include at least one of berberine or dihydroberberine. The composition may be administered in encapsulated or in a powdered form. The composition may be administered as a food, drink, capsule, food additive, drink additive, powder, etc.

In various implementations, the composition may be administered to cause blood glucose levels to decrease and/or be maintained in a healthy range of values.

In various implementations, a composition for improving performance and strength may include approximately 0.2 g to approximately 10 g of beta-hydroxybutyrate (e.g., a beta-hydroxybutyrate salt) and at least approximately 5 mg of cannabidiol. It is unexpected that cannabidiol would increase performance and strength.

Implementations may include one or more of the following features. The amount of cannabidiol may include less than approximately 300 mg of cannabidiol. The beta-hydroxybutyrate may include approximately 95 weight percent to approximately 100 weight percent of R-beta-hydroxybutyrate and less than approximately 5 weight percent of L-beta-hydroxybutyrate. The beta-hydroxybutyrate may include a beta-hydroxybutyrate salt. The beta-hydroxybutyrate may include a beta-hydroxybutyrate salt and a polymer of beta-hydroxybutyrate. The beta-hydroxybutyrate may include a beta-hydroxybutyrate salt and an ester of beta-hydroxybutyrate. The combination of the beta-hydroxybutyrate salt along with the polymer or ester of beta-hydroxybutyrate and cannabidiol may quickly increase ketone levels and the polymer of beta-hydroxybutyrate and cannabidiol may provide a more sustained response (e.g., which may require fewer dosages and/or lower dosages). The combination of being able to quickly increase ketone levels to start fat burning while maintaining ketone levels with the polymer or ester of beta-hydroxybutyrate may provide a greater performance and/or strength impact than the impact of each component individually. The composition may include a fatty acid or ester thereof (e.g., short chain, long chain, and/or medium chain fatty acids or esters thereof). The composition may include approximately 0.5 g to approximately 10 g of amino acid. The addition of an amino acid such as leucine may increase the impact of the other components greater than expected to provide greater performance and/or strength. The composition may include at least one of berberine or dihydroberberine. The composition may be administered in encapsulated or in a powdered form. The composition may be administered as a food, drink, capsule, food additive, drink additive, powder, etc.

In various implementations, the composition may be administered to cause increased strength and/or performance.

In various implementations, a composition may be provided that includes approximately 0.2 g to approximately 10 g of R-beta-hydroxybutyrate and at least approximately 5 mg of cannabidiol.

Implementations may include one or more of the following features. The composition may include fatty acids or esters thereof and/or amino acids such as leucine. The composition may include dihydroberberine. The composition may include flavor additives to increase user satisfaction. The composition may include other described compounds. The compound may be administered in healthy individuals to increase and/or maintain the health of the individual as described.

The composition may include approximately 0.2 g to approximately 10 g of beta-hydroxybutyrate (e.g., a beta-hydroxybutyrate salt) and at least approximately 5 mg of cannabidiol and administration may improve and/or maintain a health of an individual.

The composition may include approximately 0.2 g to approximately 10 g of R-beta-hydroxybutyrate (e.g., a beta-hydroxybutyrate salt) and at least approximately 5 mg of cannabidiol and administration may improve and/or maintain a health of an individual.

The composition may include a pharmaceutically effective amount of beta-hydroxybutyrate (e.g., a beta-hydroxybutyrate salt) and a pharmaceutically effective amount of cannabidiol and administration may improve a health of an individual.

The composition may include approximately 0.2 g to approximately 10 g of beta-hydroxybutyrate (e.g., a beta-hydroxybutyrate salt) and at least approximately 5 mg of cannabidiol and administration improve a cognitive function of an individual.

The composition may include approximately 0.2 g to approximately 10 g of beta-hydroxybutyrate (e.g., a beta-hydroxybutyrate salt) and at least approximately 5 mg of cannabidiol and administration may improve a body composition and/or performance of an individual.

The composition may include approximately 0.2 g to approximately 10 g of beta-hydroxybutyrate (e.g., a beta-hydroxybutyrate salt) and at least approximately 5 mg of cannabidiol and administration may decrease immune function of an individual.

The composition may include approximately 0.2 g to approximately 10 g of beta-hydroxybutyrate (e.g., a beta-hydroxybutyrate salt) and at least approximately 5 mg of cannabidiol and administration may inhibit progression and/ or development of diabetes in an individual by administering a pharmaceutically effective amount of the first composition as described herein.

The composition may include approximately 0.2 g to approximately 10 g of beta-hydroxybutyrate (e.g., a beta-hydroxybutyrate salt) and at least approximately 5 mg of cannabidiol and administration may treat substance abuse in an individual.

The composition may include approximately 0.2 g to approximately 10 g of beta-hydroxybutyrate (e.g., a beta-hydroxybutyrate salt) and at least approximately 5 mg of cannabidiol and administration may of inhibiting and/or reducing symptoms from one or more neurodegenerative diseases in an individual.

EXAMPLES

Example 1

4 subjects were administered 10 mg of sodium D,L-beta-hydroxybutyrate and their blood ketone level in mmol/dL was tested after administration, 30 minutes, 60 minutes, 90 minutes, 120 minutes, and 180 minutes after administration. Each subject was also subsequently studied after administration of 10 g of sodium R-beta-hydroxybutyrate and 5 g of sodium R-beta-hydroxybutyrate. As illustrated in FIG. 1, on average, administration of 5 mg of sodium R-beta-hydroxybutyrate produced approximately the same blood ketone level in a subject after 30 minutes, 60 minutes, 90 minutes, 120 minutes, and 180 minutes as 10 g of D,L-beta-hydroxybutyrate.

Example 2

Three subjects were administered 10 grams of medium chain triglycerides and 8 grams of beta-hydroxybutyrate and blood beta-hydroxybutyrate concentration was monitored over time. The same subjects were later administered 10 grams of short chain triglycerides and 8 grams of beta-hydroxybutyrate and blood beta-hydroxybutyrate concentration was monitored. FIG. 2 illustrates an average blood ketone concentration (mmol/L) for the subjects after administration, after 30 minutes, after 60 minutes, after 90 minutes, after 120 minutes, and after 180 minutes. As illustrated in FIG. 2, administration of the beta-hydroxybutyrate with a short chain compound (illustrated in red bars or the second bar in each set), such as short chain triglyceride, caused greater elevation of blood ketone levels than administration of a similar amount of medium chain compound (illustrated in the blue bars or first bar in each set) at least after administration, after 30, 60, 90 minutes, and 180 minutes. Thus, administration of short chain compounds (e.g., fatty acids and/or triglycerides) may unexpectedly allow a smaller weight amount, when compared to medium chain compounds, to be administered to produce the same result (e.g., blood ketone level, weight loss, weight management, etc.) and/or allow greater results (e.g., when compared with similar amount of medium chain compounds).

Example 3

Figure 3:
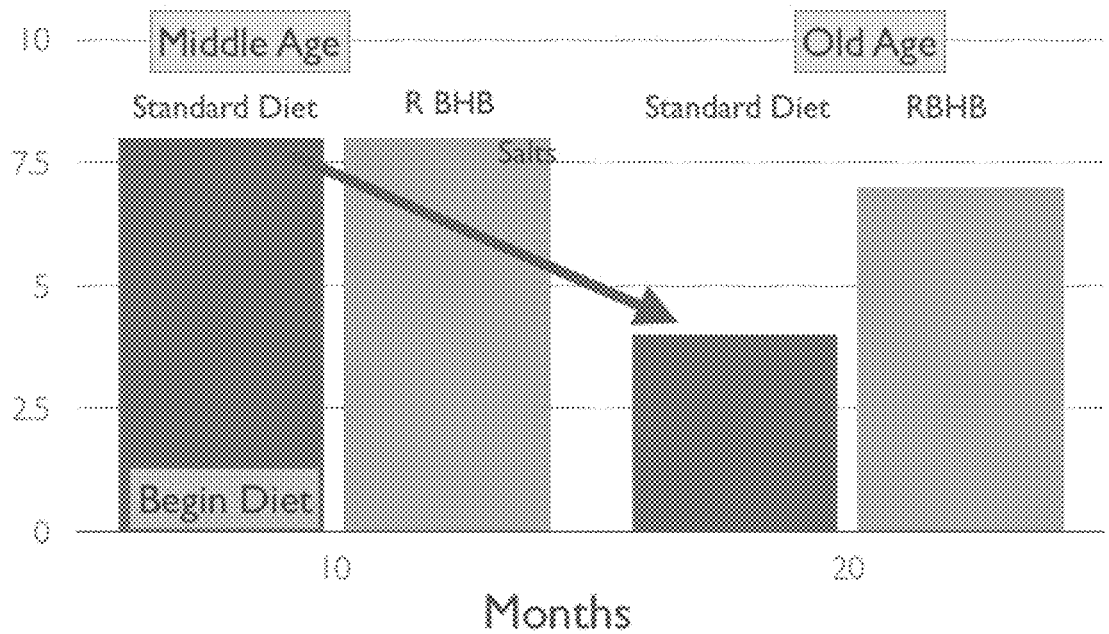
FIG. 3 illustrates a chart including lifespan of rats subject to an implementation of an administration of R-beta-hydroxybutyrate.

Sixteen rats (Fischer 344 rats) were studied for the effect of R-beta-hydroxybutyrate on lifespan. A first grouping of eight rats were fed an equivalent to a low-fat standard American diet and a second grouping of eight rats were fed the same equivalent to a low-fat standard American diet and supplemented with R-beta-hydroxybutyrate salt (e.g., sodium R-beta-hydroxybutyrate). The second grouping of rats were supplemented with the R-beta-hydroxybutyrate salt at middle age. FIG. 3 illustrates the average lifespans of the groupings of rats. As illustrated, at 20 months approximately half of the first grouping of rats died on the standard diet while only 12.5% of the second grouping of rats had died at 20 months. Thus, the supplementation of rats diets with R-beta-hydroxybutyrate increased lifespan for approximately in at least approximately 38.5% of the rats. Since the rat study was performed as an approximation of impact in humans, the addition of R-beta-hydroxybutyrate to a standard American low-fat diet may increase lifespan.

Example 4

An individual with Parkinson's disease was tested for motor function with and without administration of approximately 10 g of R-beta-hydroxybutyrate salt. The testing included a right-eye visual and motor performance apparatus to track motor function through eye movements.

Figure 4:
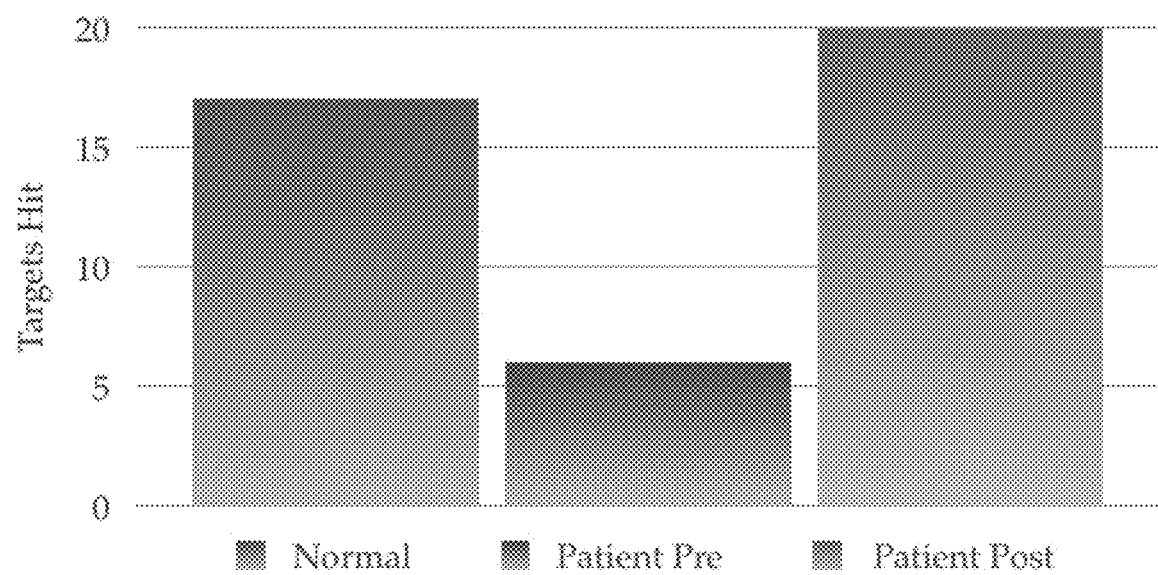
FIG. 4 illustrates a chart illustrating the results of motor skill testing following an implementation of an example administration protocol.

FIG. 4 illustrates chart illustrating the results of the motor skill testing following an example implementation of administration of R-beta-hydroxybutyrate. FIG. 4 illustrates average results for a similar non-Parkinson's population, the patient pre-administration of R-beta-hydroxybutyrate, and the patient post-administration of R-beta-hydroxybutyrate. As illustrated, the administration of R-beta-hydroxybutyrate increased motor function (e.g., approximately 30 minutes after administration of the R-beta-hydroxybutyrate).

Example 5

Figures 5A, 5B:
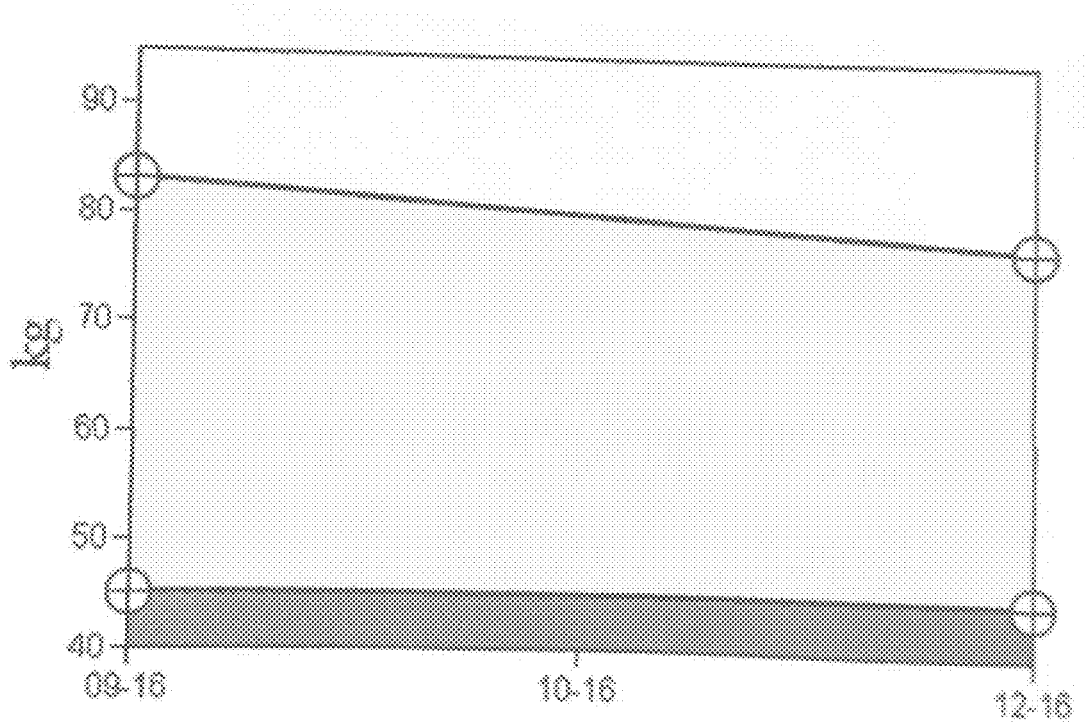
FIG. 5A illustrates a chart illustrating fat loss results following an implementation of an example administration protocol.
FIG. 5B illustrates a chart illustrating fat mass and lean mass results following an implementation of an example administration protocol.

An individual was administered 5 g of R-beta-hydroxybutyrate twice daily for 3 months. Xray absorptiometry was performed to determine the impact of the administration of R-beta-hydroxybutyrate on fat loss. FIG. 5A illustrates a chart that shows the results after 3 months of administration. As illustrated, the individual experienced a greater than approximately 10% decrease in fat mass. FIG. 5B illustrates that the fat loss was sustained while maintaining lean mass. Thus, the R-beta-hydroxybutyrate may cause weight loss through fat loss rather than lean mass (e.g., muscle mass).

Example 6

Figure 6:
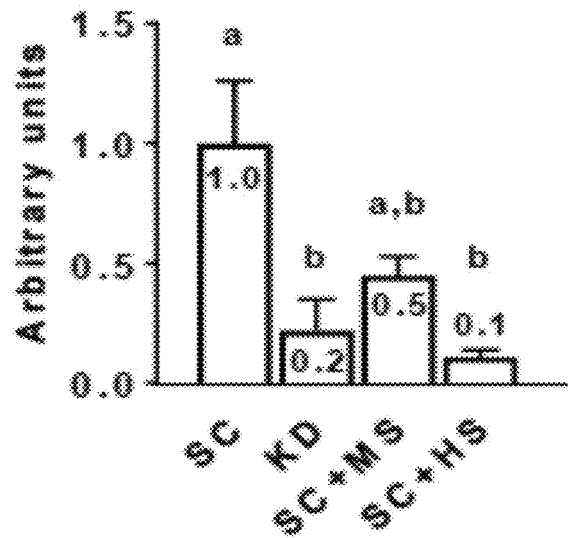
FIG. 6 illustrates a chart illustrating LPL levels in rats following an implementation of an example administration protocol.

A first grouping of 10 rats (labeled SC) were given a standard diet, a second grouping of 10 rats (labeled KD) were given a ketogenic diet, a third grouping of 10 rats (labeled SC+MS) were on the standard diet but given a first dosage of R-beta-hydroxybutyrate salt (e.g., equivalent to 5 g) and a fourth grouping was on the standard iet but given a second dosage of R-beta-hydroxybutyrate salt (e.g., equivalent to 10 g). FIG. 6 illustrates the average Lipoprotien lipase (LPL) in the rats. Since LPL is needed to transport fat into adipose tissue, lowering LPL levels would inhibit fat storage and encourage usage of fat storages. As illustrated, supplementation of a standard diet with even lower dosages of R-beta-hydroxybutyrate decreases LPL levels and thus inhibits fat storage.

Example 7

An individual with high C-reactive protein, which is associated with inflammation, was administered R-beta-hydroxybutyrate. After administration, the C-reactive protein levels were substantially reduced (e.g., 62.5 to 4.4). In addition, fasting glucose was decreased (e.g., 104 to 95).

Example 8

Figure 7:
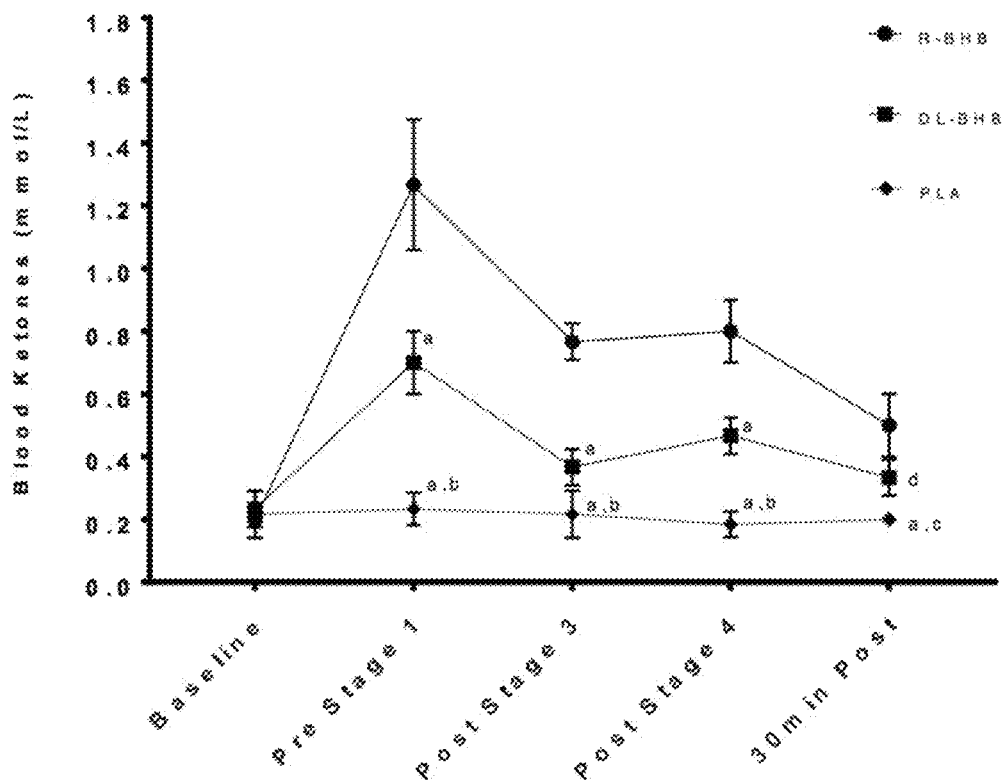
FIG. 7 illustrates a chart illustrating blood ketone levels following an implementation of an example administration protocol.
Figure 8:
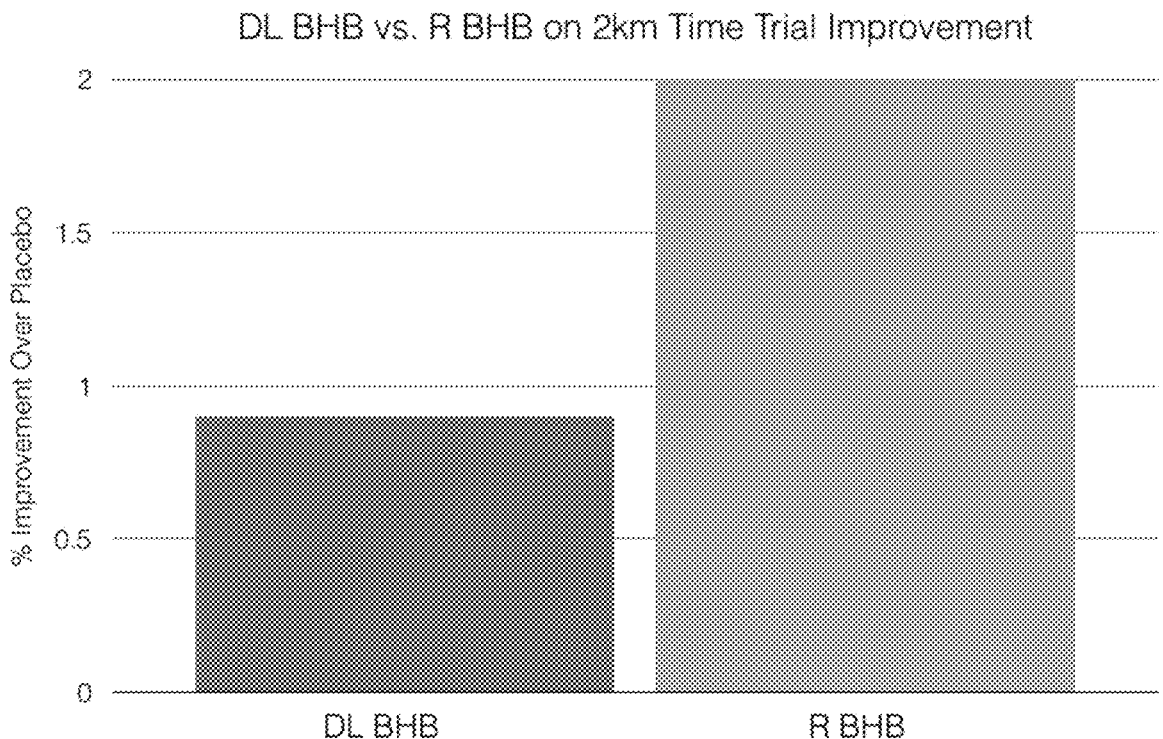
FIG. 8 illustrates a chart illustrating improvement over a placebo following an implementation of an example administration protocol.
Figure 9:
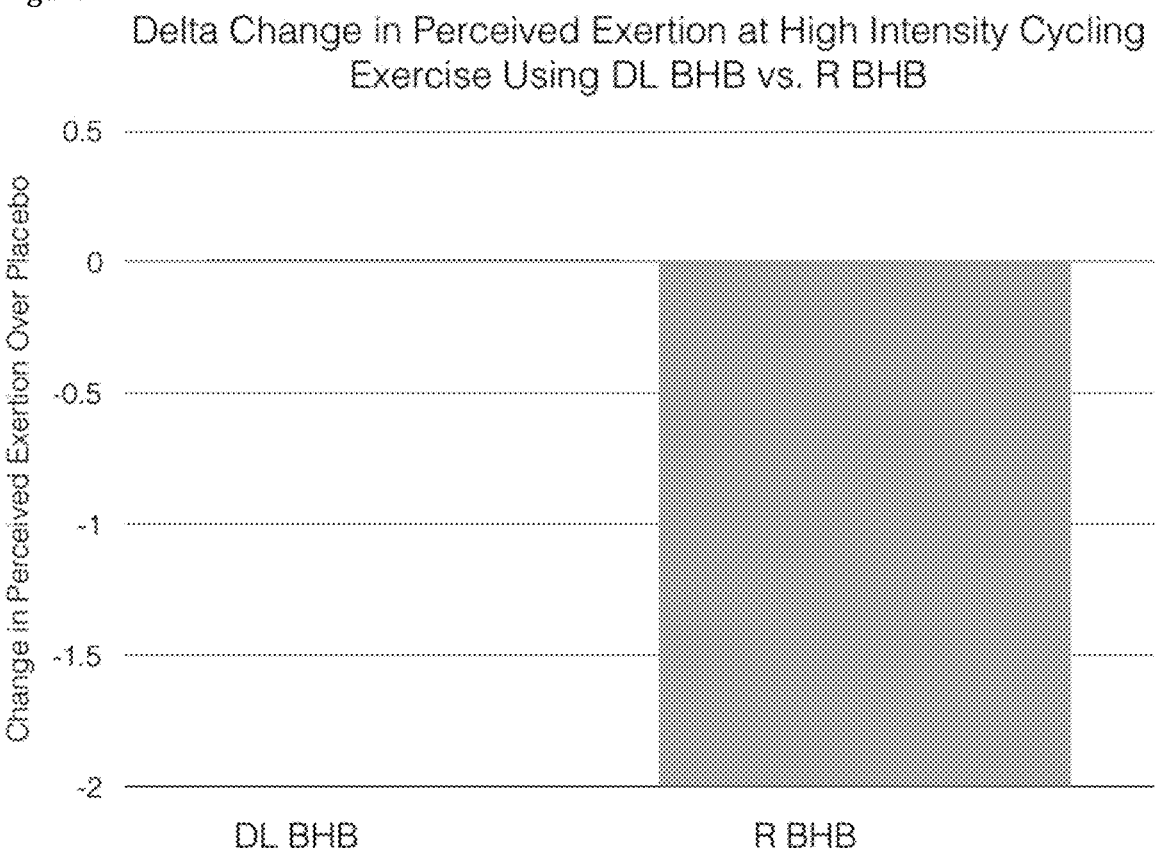
FIG. 9 illustrates a chart illustrating perceived exertion following an implementation of an example administration protocol.

Five healthy individual were given a 2 km time test (e.g., 4 cycles of low to severely intense exercise on a wingate cycle ergometer) 30 minutes after administration of a placebo, 10 g of R-beta-hydroxybutyrate, and 10 g of R-beta-hydroxybutyrate. FIG. 7 illustrates the average blood ketone levels and FIG. 8 illustrates the percentage improvement over the administration of the placebo. As illustrated, blood ketone levels unexpectedly increased more than double during administration of R-beta-hydroxybutyrate when compared with administration of D,L-beta-hydroxybutyrate. In addition, performance (e.g., improvement in time) increased by more than double during administration of R-beta-hydroxybutyrate when compared with D,L-beta-hydroxybutyrate. FIG. 9 illustrates the perceived exertion experienced by the individuals. As illustrated, the individuals did not feel an impact in perceived exertion after administration with D,L-beta-hydroxybutyrate as compared with the perceived exertion improvement experienced after administration of R-beta-hydroxybutyrate. Thus, the R-beta-hydroxybutyrate has an unexpectedly impact on ketone levels and performance.

Example 9

Individuals were given a standard diet or ketogenic diet. Some individuals were administered R-beta-hydroxybutyrate (e.g., 10 g). R-beta-hydroxybutyrate was able to numerically increase superoxide dismutase 2 levels (SOD) in the brain which indicates greater antioxidant capacity in the brain.

Example 10

Figure 10:
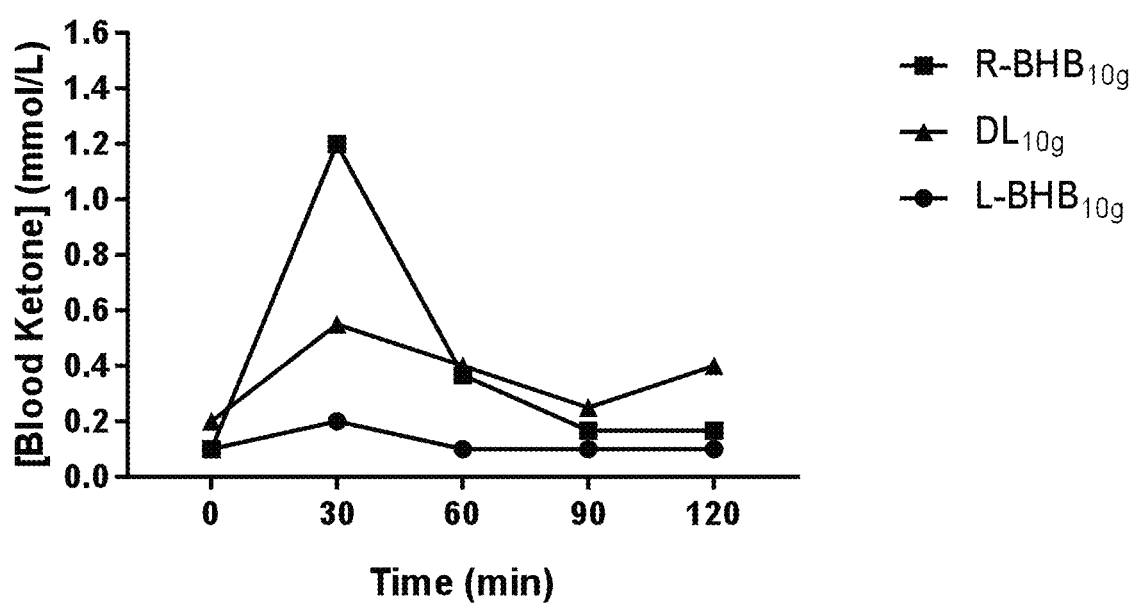
FIG. 10 illustrates a chart illustrating blood ketone levels following an implementation of an example administration protocol.
Figure 11:
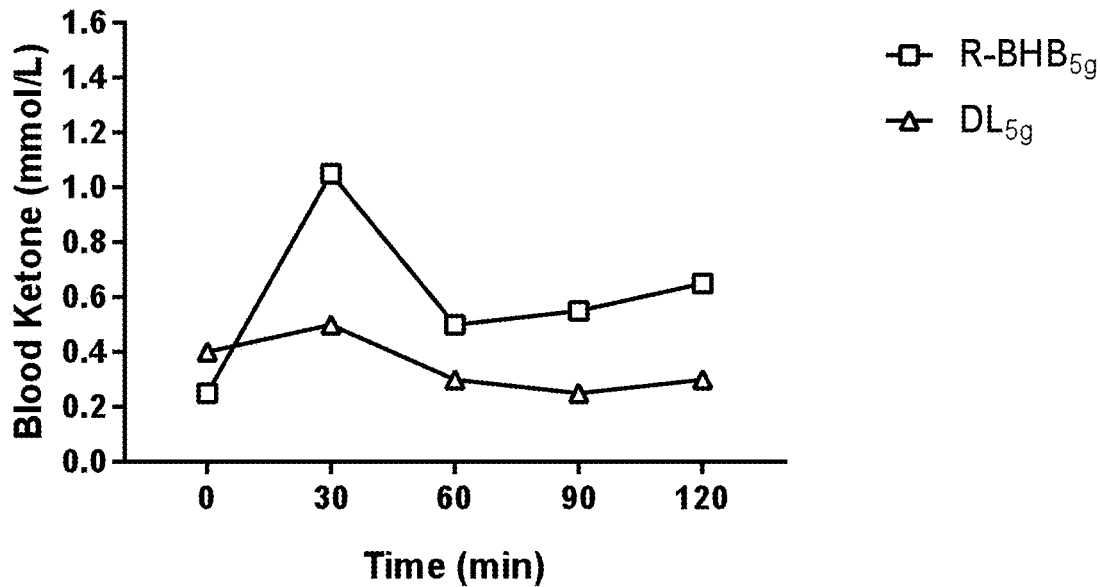
FIG. 11 illustrates a chart illustrating blood ketone levels following an implementation of an example administration protocol.

Individuals were 5 g or 10 mg of R-beta-hydroxybutyrate, L-beta-hydroxybutyrate, or D,L-beta-hydroxybutyrate and blood ketone levels were measured. FIGS. 10 and 11 illustrate the measured blood ketone levels. As illustrated, administration of R-beta-hydroxybutyrate may decrease ketone levels (see e.g., FIGS. 11A and 11B). The reduction of ketone levels occurs even when R-beta-hydroxybutyrate is administered at a dosage of less than 10 g (e.g., approximately 5 g). In addition, unexpectly (e.g., since it was expected that both the D and L forms of R-beta-hydroxybutyrate behaved in a similar manner), administration of L-beta-hydroxybutyrate does not decrease blood ketones. Furthermore, unexpectedly, even D,L-beta-hydroxybutyrate does not lower blood ketone levels to the same extent as R-beta-hydroxybutyrate. This indicates that L-beta-hydroxybutyrate may block some of the impact of R-beta-hydroxybutyrate, which is unexpected.

Example 11

Figure 12A:
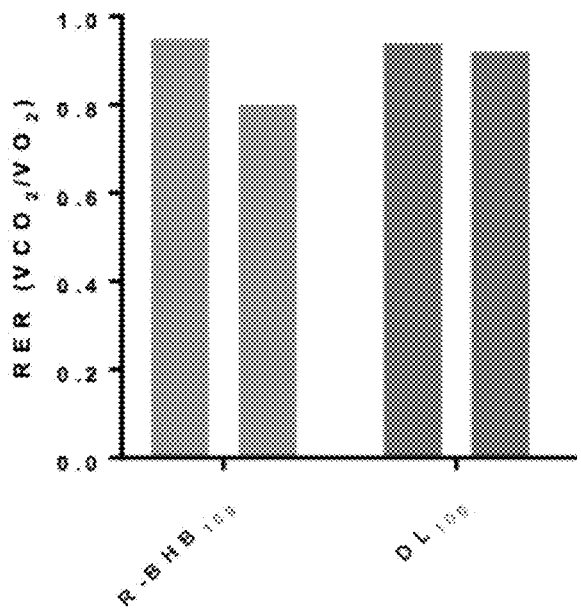
FIG. 12A illustrates a chart illustrating RER levels following an implementation of an example administration protocol.
Figure 12B:
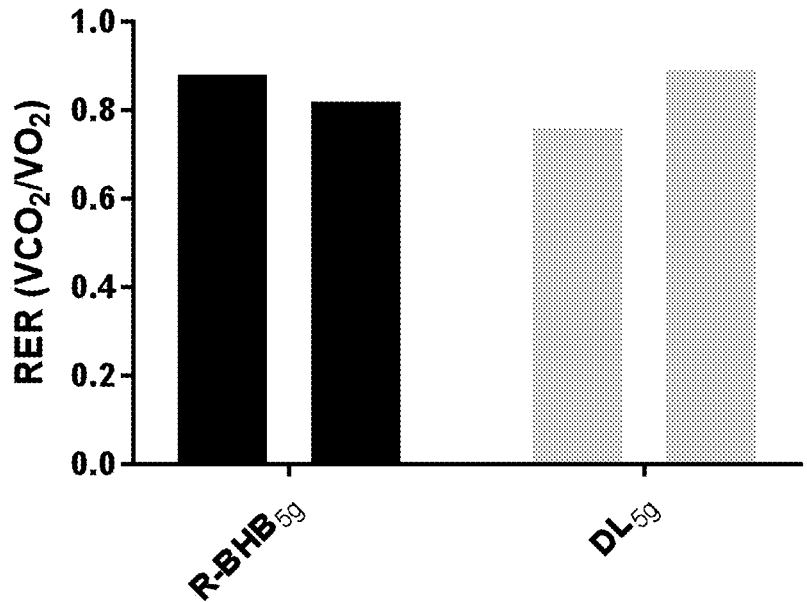
FIG. 12B illustrates a chart illustrating RER levels following an implementation of an example administration protocol.

10 subjects were administered approximately 5 g or 10 g of D,L-beta-hydroxybutyrate or R-beta-hydroxybutyrate, and Respiratory exchange ratio was examined (RER, a ratio of carbon dioxide/oxygen). Generally, a ratio of 1.0 indicates that 100% carbohydrate is used as fuel and at 0.7, 100% fat is used as fuel. As illustrated in FIG. 12A, at 10 g, R-beta-hydroxybutyrate administration reduces RER approximately 3× more than D,L-beta-hydroxybutyrate. As illustrated in FIG. 12B, 5 g of R-beta-hydroxybutyrate is capable of achieving a result that even more D,L-beta-hydroxybutyrate is unable to (e.g., D,L-beta-hydroxybutyrate increases RER by 17% rather than decreasing RER).

Example 12

Figure 13C:
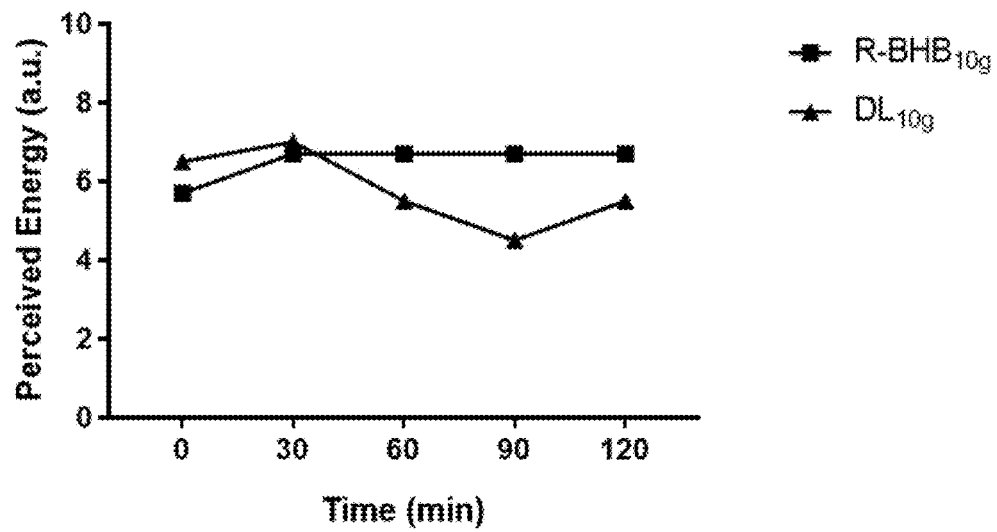
FIG. 13C illustrates a chart illustrating perceived energy following an implementation of an example administration protocol.

Individuals were administered 5 g-10 g of D,L-beta-hydroxybutyrate or R-beta-hydroxybutyrate and tested for perceived hunger, satiety, and perceived energy. FIGS. 13A-13C illustrates the results of the testing. FIG. 13A illustrates perceived hunger, FIG. 13B illustrates perceived satiety, and FIG. 13C illustrates perceived energy. As illustrated in FIG. 13B, at 30 minutes post consumption R-beta-hydroxybutyrate improved satiety levels 2.3× better than DL-beta-hydroxybutyrate relative to baseline levels. As illustrated in FIG. 13C, R-beta-hydroxybutyrate improved perceived energy from 0 to 30 minutes post consumption by double that of D,L-beta-hydroxybutyrate. R-beta-hydroxybutyrate sustained elevated perceived energy levels from 0 minutes at 60, 90, and 120 minutes post consumption, as opposed to D,L-beta-hydroxybutyrate. As illustrated, R-beta-hydroxybutyrate was able to raise perceived energy by 18% and sustain it for 2 hours post ingestion (e.g., more than 2 times greater than the peak value of increase with the DL-beta-hydroxybutyrate)

Example 13

5 young (20s) resistance trained males lifting 50% of their 1-RM on Bench Presses were tested before and after administration of 5 g of R-beta-hydroxybutyrate or D,L-beta-hydroxybutyrate. FIGS. 14A-B illustrate the results of the testing. As illustrated, R-beta-hydroxybutyrate administration resulted in an 11% increase, while DL-beta-hydroxybutyrate administration resulted in only a 2% decrease. Thus, R-beta-hydroxybutyrate experienced a greater than expected impact when compared with D,L-beta-hydroxybutyrate.

The individuals were also tested for power. FIG. 14C illustrates the results of the testing (e.g., averages of power measurements). As illustrated, R-beta-hydroxybutyrate administration increased minimum power by 26%, while the DL-beta-hydroxybutyrate administration raised power by 2%.

Example 14

Individuals were tested for mental acuity before and after administration of 5-10 g of R-beta-hydroxybutyrate or D,L-beta-hydroxybutyrate. Circular Tracking testing (e.g., to assess their cognitive function) was performed and administration of DL-beta-hydroxybutyrate (e.g., 10 g) caused no improvement while the R-beta-hydroxybutyrate (e.g., 10 g) administration caused approximately 3% improvement in tracking accuracy. Vertical Tracking testing (e.g., to assess their cognitive function) was performed and administration of D,L-beta-hydroxybutyrate (e.g., 10 g) improved performance by 4.6%, while the administration of R-beta-hydroxybutyrate (e.g., 10 g) improved performance by 13.8%, which is approximately 3 times greater improvement. Horizontal Saccades testing was performed (e.g., a saccade is one eye movement and known to become significantly slower if cognitive function declines and improve if cognitive function improves). In the horizontal saccades testing, performance improvements were 4 times greater with the administration of R-beta-hydroxybutyrate (e.g., 5 g) than with administration of D,L-beta-hydroxybutyrate (e.g., 13.8% vs.

3.2%). Processing speed testing was performed (e.g., processing speed is considered a true measure of cognitive performance). Administration of R-beta-hydroxybutyrate (e.g., 5 g) improved processing speed by 27.7% and only approximately 18% with administration of the DL-beta-hydroxybutyrate (e.g., 5 g). Response accuracy was also tested. Administration of R-beta-hydroxybutyrate (e.g., 5 g) increased accuracy by 37 percentage points when compared to 12.7% when DL-beta-hydroxybutyrate was administered.

Thus, administration of R-beta-hydroxybutyrate increased mental acuity more than a similar amount of D,L-beta-hydroxybutyrate. In fact, as the testing revealed, the administration of R-beta-hydroxybutyrate increased mental acuity often by than double when compared with a similar amount of D,L-beta-hydroxybutyrate.

Example 15

Figure 15:
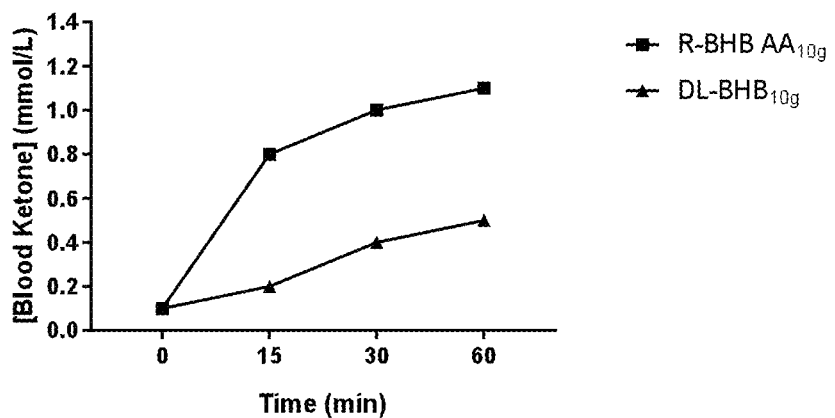
FIG. 15 illustrates a chart illustrating blood ketone levels following an implementation of an example administration protocol.

The compound for administration was prepared to include an R-beta-hydroxybutyrate amino acid complex. An R-beta-hydroxybutyrate Agmatine complex was prepared and an R-beta-hydroxybutyrate Arginine complex was prepared. FIG. 15 illustrates the average blood ketone levels achieved with the R-beta-hydroxybutyrate amino acid complex (e.g., an average of both complexes) when compared with D,L-beta-hydroxybutyrate. As illustrated, blood ketone levels are not only more than double the blood ketone levels achieved with the same quantity of D,L-beta-hydroxybutyrate as R-beta-hydroxybutyrate amino acid complex (e.g., 10 g), but they are more than an additive result of a similar amount of R-beta-hydroxybutyrate and amino acid.

Use of the R-beta-hydroxybutyrate amino acid complex may reduce the amount of cation delivered (e.g. since the complex may deliver the R-beta-hydroxybutyrate rather than a R-beta-hydroxybutyrate salt). The reduction of this cation may decrease side effects (e.g., from increased sodium, potassium, and/or magnesium intake), increase user satisfaction, and/or increase the population that can tolerate the administration of R-beta-hydroxybutyrate (e.g., since some individuals may not be capable of increasing loads of these cations due to underlying diseases and/or disorder). The use of the R-beta-hydroxybutyrate amino acid complex may also allow a higher yield of R-beta-hydroxybutyrate to be administered (90.8% R-beta-hydroxybutyrate, 5% amino acid) when compared with a similar weight of R-beta-hydroxybutyrate salt (e.g., average of 83% yield for BHB sodium).

Example 16

Figure 16:
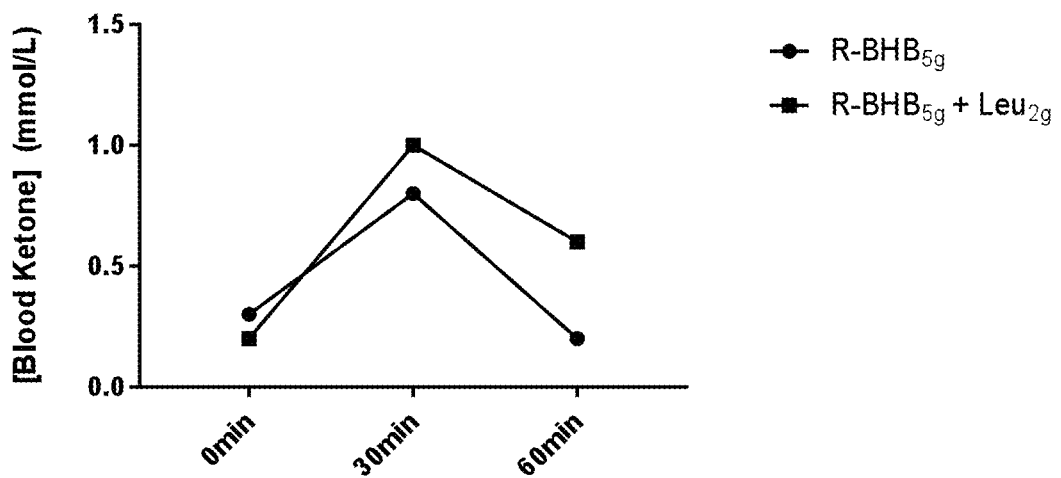
FIG. 16 illustrates a chart illustrating blood ketone levels following an implementation of an example administration protocol.

A composition for administration may include R-beta-hydroxybutyrate and an amino acid, such as Leucine. The R-beta-hydroxybutyrate and leucine maybe complexed and/ or mixed together for administration. The R-beta-hydroxybutyrate and leucine may be administered separately but approximately concurrently. FIG. 16 illustrates the blood ketone levels after administration of R-beta-hydroxybutyrate (5 g) and leucine (2 g). As illustrated, the administration of R-beta-hydroxybutyrate and leucine causes greater elevation of blood ketone levels than the administration of R-beta-hydroxybutyrate (5 g). The administration of R-beta-hydroxybutyrate and leucine causes greater elevation of blood ketone levels than merely the additive effect of similar quantities of R-beta-hydroxybutyrate and leucine administered separately.

Example 17

A composition for administration is prepared by mixing approximately 0.2 g of beta-hydroxybutyrate and approximately 5 mg of cannabidiol. The composition is orally administered as a food, drink, or capsule.

Example 18

A composition for administration is prepared by mixing approximately 0.2 g of beta-hydroxybutyrate and approximately 300 mg of cannabidiol. The composition is orally administered as a food, drink, or capsule.

Example 19

A composition for administration is prepared by mixing approximately 5 g of beta-hydroxybutyrate and approximately 5 mg of cannabidiol. The composition is orally administered as a food, drink, or capsule.

Example 20

A composition for administration is prepared by mixing approximately an approximately 1 to 1 ratio of R-beta-hydroxybutyrate (e.g., which may include less than 10 weight percent L-beta-hydroxybutyrate) to cannabidiol. The composition is orally administered as a food, drink, or capsule.

Example 21

A composition for administration is prepared by mixing approximately 10 g of beta-hydroxybutyrate and approximately 300 mg of cannabidiol. The composition is orally administered as a food, drink, or capsule.

Example 22

A composition for administration is prepared by mixing approximately 10 g of beta-hydroxybutyrate and approximately 1500 mg of cannabidiol. The composition is orally administered as a food, drink, or capsule.

Example 23

A composition for administration is prepared by mixing an approximately 1:1:1 to 1:2:1 ratio of beta-hydroxybutyrate to cannabidiol to fatty acid or ester thereof. The composition is orally administered as a food, drink, or capsule.

Example 24

A composition for administration is prepared by mixing approximately 5 g of beta-hydroxybutyrate, approximately 5 mg of cannabidiol, and leucine. The composition is orally administered as a food, drink, or capsule.

Example 25

A composition for administration is prepared by mixing approximately 10 g of beta-hydroxybutyrate, approximately 100 mg of cannabidiol, and leucine. The composition is orally administered as a food, drink, or capsule.

Example 26

A composition for administration is prepared by mixing approximately 5 g of beta-hydroxybutyrate salt, 10 g of a polymer of beta-hydroxybutyrate, and approximately 5 mg of cannabidiol. The composition is orally administered as a food, drink, or capsule.

End of Examples

In some implementations, one or more additives may be included in the composition, such as flavorings (e.g., natural and/or artificial), vitamins, minerals, binders, and/or any other appropriate additive.

The described compositions may be administered via any appropriate administration method. For example, the described compositions may be administered enterally and/or parenterally. In some implementations, the described composition may be administered via a tablet and/or capsule. The described composition may be provided in a powdered form that allows the described composition to be sprinkled on food, mixed with a liquid to provide a beverage, and/or directly administered. The described composition may be provided in gel form. The compounds in the composition may be mixed, coupled to each other, and/or provided separately. For example, the composition may include beta-hydroxybutyrate coupled to another compound (e.g., beta-hydroxybutyrate ester and/or amino acid). In some implementations, the beta-hydroxybutyrate and one or more other compounds may be provided separately (e.g., in pills). An individual may sequentially and/or concurrently be administered (e.g., swallow pills) the beta-hydroxybutyrate and other compounds.

The described compositions may be administered on an administration protocol to cause weight loss and/or maintain a weight of an individual; elevate and/or maintain blood ketone levels; increase and/or maintain ketosis; and/or improve glucose tolerance (e.g., fasting glucose levels may be reduced and/or glucose metabolism may be improved), in some implementations. For example, the described compositions may be administered once a day, via an extended release preparation, and/or multiple times a day (e.g., 1 to 5 times a day, 2 to 5 times a day, 3 to 5 times a day, etc.). The described composition may replace other pharmaceuticals or dietary supplements taken to promote weight loss, maintain a weight, promote ketosis, elevate blood ketone levels and/or be utilized in combination with one or more other pharmaceuticals or dietary supplements, as appropriate. The described composition may replace other pharmaceuticals or dietary supplements taken for improving glucose tolerance, such as metaformin, and/or be utilized in combination with one or more other pharmaceuticals or dietary supplements, as appropriate, in some implementations.

In various implementations, the described composition(s) (e.g., butyrate, beta-hydroxybutyrate, R-beta-hydroxybutyrate, related compounds, and/or one or more other compounds) may include one or more of the described components, equivalent(s) of the described component(s), derivatives of the described component(s), complex(es) of the described component(s), salt(s) of the described component(s), and/or combinations thereof.

In various implementations, a pharmaceutically effective amount of one or more of the described composition(s) may be administered. Administration of the pharmaceutically effective amount may induce and/or maintaining ketosis; maintaining and/or promoting weight loss; increase mental processes (e.g., acuity including cognitive functioning, mood, energy, alertness, focus, performance, effects of aging, etc.); improve and/or maintain body composition; function as a therapeutic for one or more of the described conditions or disorders (e.g., treat neurological disorders); and/or combinations thereof.

Although various types of increases in mental acuity have been described, other features of mental acuity such as memory, focus, concentration, and/or understanding (e.g., speed of processing, accuracy of processing) may be increased by administration of an effective amount of the composition that includes R-beta-hydroxybutyrate.

Although a subject and/or an individual have been described as a human, a subject and/or individual may be a person or a group of people. Although various described systems and processes have been described as a being administered in humans, the described systems and processes may be administered to other mammals, such as rats, dogs, etc.

In various implementations, beta-hydroxybutyrate may administered simultaneously and/or sequentially with one or more other compounds (e.g., short chain, medium chain, and/or long chain fatty acids). For example, beta-hydroxybutyrate and/or one or more other compounds may be delivered mixed in a powdered, liquid, gel, and/or other appropriate form. In some implementations, the beta-hydroxybutyrate and/or one or more other compounds may be administered via pills, tablets, capsules, other oral administration forms, intravenously, nasal sprays, sublingual tabs/strips, or topical delivery, rectal, other appropriate administration forms, and/or combinations thereof.

Although the term beta-hydroxybutyrate is the terminology used in the described implementations, beta-hydroxybutyrate is also referred to as beta-hydroxybutyrate, (R)-3-Hydroxybutyric acid, (R)-3-Hydroxybutanoic acid, (3R)-3-hydroxybutanoic acid, (R)-3-Hydroxybutanoate, (R)-(−)-3-Hydroxybutyric acid, (R)-(−)-beta-Hydroxybutyric acid, 3-D-hydroxybutyrate, BHIB, BHB, 3-delta-hydroxybutyrate, delta-3-hydroxybutyrate, 3-D-hydroxybutyric acid, D-3-hydroxybutyric acid, 3R-hydroxy-butanoic acid, delta-beta-hydroxybutyrate, D-3-hydroxybutyrate, D-(−)-3-hydroxybutyrate, delta-3-hydroxybutyric acid, (−)-3-Hydroxybutyric acid, D-beta-hydroxybutyrate, (R)-(−)-b-Hydroxybutyrate, (R)-beta-Hydroxybutyric acid, delta-(−)-3-hydroxybutyrate, (R)-3-hydroxybutyrate, (R)-beta-Hydroxybutanoic acid, (R)-(−)-beta-hydroxybutyrate, (−)-3-Hydroxy-n-butyric acid, (R)-(−)-b-Hydroxybutyric acid, Butanoic acid, 3-hydroxy-, (R)-Butyric acid, 3-hydroxy-, D-(−)-(R)-3-82578-46-9, beta-D-Hydroxybutyric acid, D-beta-Hydroxybutyric acid, (3R)-3-delta-hydroxybutyric acid, 3-(R)-Hydroxybutyric acid, and/or (−)-beta-Hydroxybutyrate.

In various implementations, beta-hydroxybutyrate is described as included in a composition; administered in an amount, form, and/or schedule; and/or being in a particular form (e.g., complexed and/or coupled). R-beta-hydroxybutyrate may be utilized in the various described implementations of beta-hydroxybutyrate in the same or lower amount as the described beta-hydroxybutyrate, as appropriate.

References have been made to U.S. patent application Ser. Nos. 15/491,924; 15/491,933; U.S. Provisional Patent Application No. 62/324,794; and, U.S. Provisional Patent Application No. 62/324,798. These applications are hereby incorporated by reference to the extend that their teachings together and/or individually do not conflict with the teachings disclosed herein.

It is to be understood the implementations are not limited to particular systems or processes described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise. Thus, for example, reference to "a compound" includes a combination of two or more compounds and reference to "a beta-hydroxybutyrate" includes different types and/or combinations of beta-hydroxybutyrate. As another nonlimiting example, reference to a "cannabidiol" includes different forms and combinations of cannabidiol.

Although the present disclosure has been described in detail, it should be understood that various changes, substitutions and alterations may be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A synergistic composition for weight loss or weight management in an individual in need thereof, the composition comprising:
approximately 0.2 g to approximately 15 g of R-beta-hydroxybutyrate, wherein the R-beta-hydroxybutyrate comprises:
a first source of R-beta-hydroxybutyrate, wherein the first source of R-beta-hydroxybutyrate comprises at least one salt of R-beta-hydroxybutyrate; and
a second source of R-beta-hydroxybutyrate, wherein the second source of R-beta-hydroxybutyrate is selected from the group consisting of R-1,3-butanediol, ester of R-beta-hydroxybutyrate, oligomer of R-beta-hydroxybutyrate, polymer of R-beta-hydroxybutyrate, and R-beta-hydroxybutyrate-complex; and
at least approximately 5 mg of cannabidiol.

2. The synergistic composition of claim 1 wherein the composition is at least one of encapsulated or in a powdered form.

3. The synergistic composition of claim 1 wherein the first source of R-beta-hydroxybutyrate comprises at least one of sodium R-beta-hydroxybutyrate, magnesium R-beta-hydroxybutyrate, calcium R-beta-hydroxybutyrate, lithium R-beta-hydroxybutyrate, or potassium R-beta-hydroxybutyrate.

4. The synergistic composition of claim 1 wherein the first source of beta-hydroxybutyrate comprises a mixture of R-beta-hydroxybutyrate salts.

5. The synergistic composition of claim 1 wherein the composition comprises at least approximately 90% of R-beta-hydroxybutyrate and less than approximately 10% of L-beta-hydroxybutyrate.

6. The synergistic composition of claim 1 further comprising at least one amino acid.

7. The synergistic composition of claim 1 further comprising at least 0.5 to 10 g of at least one amino acid.

8. The synergistic composition of claim 1 further comprising at least 0.5 to 10 g of leucine.

9. The synergistic composition of claim 1 wherein the composition comprises approximately 5 mg to approximately 300 mg of cannabidiol.

10. The synergistic composition of claim 1 further comprising a pharmaceutically effective amount of fatty acid or ester thereof.

11. A synergistic composition for improving or maintaining glucose levels in an individual in need thereof, the composition comprising:
approximately 0.2 g to approximately 15 g of R-beta-hydroxybutyrate, wherein the R-beta-hydroxybutyrate comprises:
a first source of R-beta-hydroxybutyrate, wherein the first source of R-beta-hydroxybutyrate comprises at least one salt of beta-hydroxybutyrate; and
a second source of R-beta-hydroxybutyrate, wherein the second source of R-beta-hydroxybutyrate is selected from the group consisting of R-1,3-butanediol, ester of R-beta-hydroxybutyrate, oligomer of R-beta-hydroxybutyrate, polymer of R-beta-hydroxybutyrate, and R-beta-hydroxybutyrate-complex; and
at least approximately 5 mg of cannabidiol.

12. The synergistic composition of claim 11 wherein the first source of R-beta-hydroxybutyrate comprises at least one of sodium R-beta-hydroxybutyrate, magnesium R-beta-hydroxybutyrate, calcium R-beta-hydroxybutyrate, lithium R-beta-hydroxybutyrate, or potassium R-beta-hydroxybutyrate.

13. The synergistic composition of claim 11 wherein the comprises at least approximately 90% of R-beta-hydroxybutyrate and less than approximately 10% of L-beta-hydroxybutyrate.

14. The synergistic composition of claim 11 further comprising at least one amino acid.

15. The synergistic composition of claim 11 further comprising at least one fatty acid or ester thereof.

16. A method of weight loss or weight management in an individual in need thereof, the method comprising administering a synergistic composition comprising approximately 0.2 g to approximately 15 g of R-beta-hydroxybutyrate, wherein the R-beta-hydroxybutyrate comprises: a first source of R-beta-hydroxybutyrate, wherein the first source of R-beta-hydroxybutyrate comprises at least one salt of R-beta-hydroxybutyrate; and a second source of R-beta-hydroxybutyrate, wherein the second source of R-beta-hydroxybutyrate is selected from the group consisting of R-1,3-butanediol, ester of R-beta-hydroxybutyrate, oligomer of R-beta-hydroxybutyrate, polymer of R-beta-hydroxybutyrate, and R-beta-hydroxybutyrate-complex; and at least approximately 5 mg of cannabidiol.

17. The method of claim 16 wherein administration of the pharmaceutically effective amount of R-beta-hydroxybutyrate and the pharmaceutically effective amount of cannabidiol improves or maintains glucose levels in an individual.

18. The method of claim 16 wherein administration of the pharmaceutically effective amount of R-beta-hydroxybutyrate and the pharmaceutically effective amount of cannabidiol induces or maintains ketosis in an individual.

* * * * *